(12) United States Patent
Alper et al.

(10) Patent No.: US 9,273,307 B2
(45) Date of Patent: Mar. 1, 2016

(54) GLOBAL TRANSCRIPTION MACHINERY ENGINEERING

(71) Applicant: Massachusetts Institute of Technology, Cambridge, MA (US)

(72) Inventors: Hal S. Alper, Austin, TX (US); Gregory Stephanopoulos, Winchester, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/054,631

(22) Filed: Oct. 15, 2013

(65) Prior Publication Data

US 2014/0235453 A1    Aug. 21, 2014

Related U.S. Application Data

(63) Continuation of application No. 11/238,096, filed on Sep. 28, 2005, now abandoned.

(51) Int. Cl.
| | |
|---|---|
| *C12Q 1/68* | (2006.01) |
| *C12N 15/10* | (2006.01) |
| *C12N 15/70* | (2006.01) |

(52) U.S. Cl.
CPC ........ *C12N 15/1058* (2013.01); *C12N 15/1079* (2013.01); *C12N 15/70* (2013.01); *C12Q 1/6811* (2013.01)

(58) Field of Classification Search
None
See application file for complete search history.

(56) References Cited

U.S. PATENT DOCUMENTS

| 7,138,513 B2 * | 11/2006 | Zelder et al. ............. 536/23.7 |
| 7,226,781 B1 * | 6/2007 | Belyaev ............. 435/320.1 |
| 2005/0009152 A1 | 1/2005 | Zelder et al. |

OTHER PUBLICATIONS

Mahren et al., Journal of Bacteriology (2002) vol. 184, pp. 3704-3711.*
Alper, H. et al., "Tuning genetic control through promoter engineering," *PNAS* Sep. 2005; 102(36):12678-12683.
Alper, H., "Development of Systematic and Combinatorial Approaches for the Metabolic Engineering of Microorganisms," Massachusetts Institute of Technology, Boston, USA; Jun. 2006; retrieved from the Internet at http://dspace.mit.edu/bitstream/1721.1/35134/1/71825623; pp. 237-242.
Alper, H. et al., "Global transcription machinery engineering: A new approach for improving cellular phenotype," *Metabolic Engineering* Jan. 8, 2007; retrieved from the Internet at www.sciencedirect.com; 10 pages.
Alper, H. et al., "Engineering yeast transcription machinery for improved ethanol tolerance and production," *Science* Dec. 8, 2006; 314(5805):1565-1568.
Gowrishankar, J. et al., "In vitro properties of RpoS (sigma(S)) mutants of *Escherichia coli* with postulated N-terminal subregion 1.1 or C-terminal region 4 deleted," *Journal of Bacteriology* Apr. 2003; 185(8):2673-2679.
Mahren, S. et al., "Functional Interaction of Region 4 of the Extracytoplasmic Function Sigma Factor FecI with the Cytoplasmic Portion of the FecR Transmembrane Protein of the *Escherichia coli* Ferric citrate Transport System," *Journal of Bacteriology* Jul. 2002; 184(13):3704-3711.
Wu, Wei-Hua et al., "Mutational Analysis of Yeast TFIIB: A Functional Relationship Between Ssu72 and Sub1/Tsp1 Defined by Allele-Specific Interactions with TFIIB," *Genetics* Oct. 1999; 153(2):643-652.
Yura, T. et al., "Genetic Studies of RNA Polymerase Sigma Factor in *Escherichia coli*," 1980, University of Tokyo Press, Tokyo, Japan, pp. 51-63.

* cited by examiner

*Primary Examiner* — Jim Ketter
(74) *Attorney, Agent, or Firm* — Wolf, Greenfield & Sacks, P.C.

(57) ABSTRACT

The invention relates to global transcription machinery engineering to produce altered cells having improved phenotypes.

13 Claims, 17 Drawing Sheets

```
Native   MEQNPQSQLKLLVTRGKEQGYLTYAEVNDHLPEDIVDSDQIEDIIQMINDMGIQVMEEAP 60
Round1   MEQNPQSQLKLLVTRGKEQGYLTYAEVNDLLPEDIVD-DQIEDIIQMINDMGIQVMEEAS 59
Round2   ------------------------------------------------------------
Round3   ------------------------------------------------------------
         *****************************.*******.********************.

Native   DADDLMLAENTADEDAAEAAAQVLSSVESEIGRTTDPVRMYMREMGTVELLTREGEIDIA 120
Round1   DADDLMLAENTADEDAAEAAAQVLSSVESEIGRTIDPVRMYMREMGTVELLTREGEIDIA 119
Round2   ------------------------------------------------------------
Round3   ------------------------------------------------------------
         *********************************.**************************

Native   KRIEDGINQVQCSVAEYPEAITYLLEQYDRVEAEEARLSDLITGFVDPNAEEDLAPTATH 180
Round1   KRIEDGINQVQCSVAEYPEAITYLLEQYDRVEAEEARLSDLITGFVDPNAEEDLAPTATH 179
Round2   ------------------------------------------------------------
Round3   ------------------------------------------------------------
         ************************************************************

Native   VGSELSQEDLDDDEDEDEEDGDDDSADDDNSIDPELAREKFAELRAQYVVTRDTIKAKGR 240
Round1   VGSELSQEDLDDDEDEDEEDGDDGSADDDNSIDPELAREKLAELRAQYVVTRDTIKAKGR 239
Round2   ------------------------------------------------------------
Round3   ------------------------------------------------------------
         ***********************.****************:*******************

Native   SHATAQEEILKLSEVFKQFRLVPKQFDYLVNSMRVMMDRVRTQERLIMKLCVEQCKMPKK 300
Round1   SHATAQEEFLKLSEVFKQFRLVPKQFDYLVNSMRVMMDRVRTQERLVMKLCVEQCKMPKK 299
Round2   ------------------------------------------------------------
Round3   ------------------------------------------------------------
         ********:************************************:**************

Native   NFITLFTGNETSDTWFNAAIAMNKPWSEKLHDVSEEVHRALQKLQQIEEETGLTIEQVKD 360
Round1   NFITLFTGNETSDTWFNAAIAMNKPWSEKLHDVSEEVHRALQKLQQIEEETGLTIEQVKD 359
Round2   ------------------------------------------------------------
Round3   ------------------------------------------------------------
         ************************************************************

Native   INRRMSIGEAKARRAKKEMVEANLRLVISIAKKYTNRGLQFLDLIQEGNIGLMKAVDKFE 420
Round1   INRRMSIGEAKARRAKKEMVEANLRLVISIAKKYTNRGLQFLDLIQEGNIGLMKAVDKFE 419
Round2   ------------------------------------------------------------
Round3   ------------------------------------------------------------
         ************************************************************

Native   YRRGYKFSTYATWWIRQAITRSIADQARTIRIPVHMIETINKLNRISRQMLQEMGREPTP 480
Round1   YRRGYKFSTYATWWIRQAITRSIADQARTIRIPVHMIETINKLNRISRQMLQEMGREPTP 479
Round2   ------------------------------------------------------------
Round3   ------------------------------------------------------------
         ************************************************************

Native   EELAERMLMPEDKIRKVLKIAKEPISMETPIGDDEDSHLGDFIEDTTLELPLDSATTESL 540
Round1   EELAERMLMPEDKIRKVLKIAKEPISMETPVGDDEDSHLGDFIEDTTLELPLDSATTESL 539
Round2   ------------------------------METPIGDDEDSHLGDFIEDTTLELPLDSATTESL 34
Round3   ------------------------------METPIGDDEDSLLGDFIEDTTLELPLDSATTVSL 34
                                        ****:********.******************.**

Native   RAATHDVLAGLTAREAKVLRMRFGIDMNTDYTLEEVGKQFDVTRERIRQIEAKALRKLRH 600
Round1   RAATHDVLAGLTAREAKVLRMRFGIDMNTDYTLEEVGKQFDVTRERIRQIEAKALRKLRH 599
Round2   RAATHDVLAGLTAREAKVLRMRFGIDMNTDYTLEEVGKQFDVTRERIRQIEAKALRKLRH 94
Round3   RVATHDVLAGLTARVAKVLRMRFGINMNTDYTLEEVGKQFDVTRERIRQIEAKALRKLRH 94
         *.************ .********.**********************************

Native   PSRSEVLRSFLDD 613
Round1   PSCSEVLRSFLDD 612
Round2   PSCSEVLRSFLDD 107
Round3   PSRSGVQRSFLDD 107
         **.*.*:******
```

Fig. 2D

```
Native  MEQNPQSQLKLLVTRGKEQGYLTYAEVNDHLPEDIVDSDQIEDIIQMINDMGIQVMEEAP  60
Ac1     ------------------------------------------------------------
Ac2     MEQNPQSQLKLLVTRGKE-GYLTYAEVNDHLPEDIVDSDQIEDIIQMINDMGIQVMEEAP  59
Ac3     MDQNPQSQLKLLVTRGKEQGYLTYAEVNDHLPEDIVDSDQIEDIIQMINDMGIQVMEEAP  60
Ac4     MEQNPQSQLKLLVTRGKEQGYLTYAEVNDHLPEDIVDSDQIEDIIQMINDMGIQVMEEAP  60
Ac5     MEQNPQSQLKLLVTRGKEQGYLTYAEVNDHLPEDIVDSDQIEDIIQMINDMGIQVMEEAP  60
         *:***************.******************************************

Native  DADDLMLAENTADEDAAEAAAQVLSSVESEIGRTTDPVRMYMREMGTVELLTREGEIDIA  120
Ac1     ------------------------------------------------------------
Ac2     DADDLMLAENTADEDAAEAAAQVLSSVESGVGRTTDPVRMYMREMGTVELLTREGEIDIA  119
Ac3     DADDLMLAENTADEDAAEAVAQVLSSVESEIGRTTDPVRMYMREMGTVELLTREGEIDIA  120
Ac4     DADDLMLAENTADEDAAEAAAQVLSSVESEIGRTTDPVRMYMREMGTVELLTREGEIDIA  120
Ac5     DADDLMLAENTADEDAAEAAAQVLSSVESEIGRTTDPVRMYMREMGTVELLTREGEIDIA  120
         *******************.********.:******************************

Native  KRIEDGINQVQCSVAEYPEAITYLLEQYDRVEAEEARLSDLITGFVDPNAEEDLAPTATH  180
Ac1     ------------------------------------------------------------
Ac2     KRIEDGNNQVQCSVAEYPEAITYLLEQYDRAEAEEARLSDMITGFVDPNAEEDLAPTATH  179
Ac3     KRIEDGINQVQCSVAEYPEAITYLLEQYDRVEAEEARLSDLITGFVDPNAEEDLAPTATH  180
Ac4     KRIEDGVNQVQCSVAEYPEAITYLLEQYDRVEAEEARLSDLITGFVDPNAEEDLAPTATH  180
Ac5     KRIEDGINQVQCSVAEYPEAITYLLEQYDRVEAEEARLSDLITGFVDPNAEEDLAPTATH  180
         ******.********************** *********:********************

Native  VGSELSQEDLDDDEDEDEEDGDDDSADDDNSIDPELAREKFAELRAQYVVTRDTIKAKGR  240
Ac1     ------------------------------------------------------------
Ac2     VGSELSQEDLDDDEDEDEDEVDGDDDSADDDNSIDPELAREKFAELRAQYVVTRDTIKAKGR  239
Ac3     VGSEPSQEDLDDDEDEDEEDGDDDSADDDNSIDPELAREKFAELRAQYVVTRDTIKAKGR  240
Ac4     VGSELSQEDLDDDEDEDEEDGDDDSADDDNSIDPELAREKFAELRAQYVVTRDTI-AKGR  239
Ac5     VGSELSQEDLDDDEDEDEEDGDDDSADDDNSIDPELAREKFAELRAQYVVTRDTIKAKGR  240
         ****.*******************************************.****

Native  SHATAQEEILKLSEVFKQFRLVPKQFDYLVNSMRVMMDRVRTQERLIMKLCVEQCKMPKK  300
Ac1     ------------------------------------------------------------
Ac2     SHATAQEEILKLSEVFKQFRLVPKQFDYLVNSMRVMMDHVRTQERLIMKLCVEQCKMPKK  299
Ac3     SHATAQEEILKLSEVFKQFRLVPKQFDYLVNSMRVMMDRVRTQERLIMKLCVEQCKMPKK  300
Ac4     SHATAQEEILKLSEVFKQFRLVPKQFDYLVNSMRVMMDRVRTQERLIMKLCVEQCKMPKK  299
Ac5     SHATAQEEILKLSEVFKQFRLVPKQFDYLVNSMRVMMDRVRTQERLIMKLCVEQCKMPKK  300
         *************************************:**********************

Native  NFITLFTGNETSDTWFNAAIAMNKPWSEKLHDVSEEVHRALQKLQQIEEETGLTIEQVKD  360
Ac1     ------------------------------------------------------------
Ac2     NFITLFTGNETSDTWFNAAIAMNRPWSEKLHDVSEEVHRALQKLQQIEEETGLTIEQVKD  359
Ac3     NFITLFTGNETSDTWFNAAIAMNKLWSEKLHDVSEEVHRALQKLRQIEEETGLTIEQVKD  360
Ac4     NFITLFTGNETSDTWFNAAIAMNKPWSEKLHDVSEEVHRALQKLQQIEEETGLTIEQVKD  359
Ac5     NFITLFTGNETSDTWFNAAIAMNKPWSEKLHDVSEEVHRALQKLQQIEEETGLTIEQVKD  360
         **********************:.*******************:*****************

Native  INRRMSIGEAKARRAKKEMVEANLRLVISIAKKYTNRGLQFLDLIQEGNIGLMKAVDKFE  420
Ac1     ------------------------------------------------------------
Ac2     INRRMSIGEAKARRAKKEMVEANLRLVISIAKKYTNRGLQFLDLIQEGNIGLMKAVDKFE  419
Ac3     INRRMSIGEAKARRAKKEMVEANLRLVISIAKKYTNRGLQFLDLIQEGNIGLMKAVDKFE  420
Ac4     INRRMSIGEAKARRAKKEMVEANLRLVISIAKKFTNRGLQFLDLIQEGNIGLVKAVDKFE  419
Ac5     INRRMSIGEAKARRAKKEMVEANLRLVISIAKKYTNRGLQFLDLIQEGYIGLMKAVDKFE  420
         ********************************:*************.***.********

Native  YRRGYKFSTYATWWIRQAITRSIADQARTIRIPVHMIETINKLNRISRQMLQEMGREPTP  480
Ac1     ------------------------------------------------------------
Ac2     YRRGYKFSTYATWWIRQAITRSIADQARTIRIPVHMIETINKLNRISRQMLQEMGREPTP  479
Ac3     YRRGYKFSTYATWWIRQAITRFIADQARTIRIPVHMIETINKLNRISRQMLQEMGREPTP  480
Ac4     YRRGYKFSTYATWWIRQAITRSIADQARTIRIPVHMIETIN-LNRISRQMLQEMGREPTP  478
Ac5     YRRGYKFSTYATWWIRQAITRSIADQARTIRIPVHMIETIDKLNRISRQMLQEMGREPTP  480
         ********************:*******************.*******************
```

Fig. 3B

```
Native    EELAERMLMPEDKIRKVLKIAKEPISMETPIGDDEDSHLGDFIEDTTLELPLDSATTESL 540
Ac1       ------------------------------METPIGDDEDSHLGDYIEDTTLELPLDSATTESL  34
Ac2       EELAERMLMPEDKIRKVLKIAKEPISMETPIGDDEDSHLGDFIEDTTLELPLDSATTESL 539
Ac3       EELAERMLMPEDKIRKVLKIAKEPISMETPIGDDEDSHLGDFIEDTTLELPLDSATTESL 540
Ac4       EELAERMLMQEDKIRKVLKIANEPISMETPIGDDEDSHLGDFIEDTTLELPLDSATTESL 538
Ac5       EELAERMLMPEDKIRKVLKIAKEPISMETPIGDDEDSHLGDFIEDTTLELPLDSATTESL 540
          ********.*************:*********************:***************

Native    RAATHDVLAGLTAREAKVLRMRFGIDMNTDYTLEEVGKQFDVTRERIRQIEAKALRKLRH 600
Ac1       RAATHDVLAGMTAREAKVLRMRFGIDVNTDYTLEEVGKQFDVTRERISQIEAKALRKLRH  94
Ac2       RAATHDVLAGLTAREAKVLRMRFGIDMNTDYTLEEVGKQFDVTRERIRQIEAKALRKLRH 599
Ac3       RAATHDVLAGLTAREAKVLRMRFGIDVNTDYTLEEVSKQFNVTRERIRQIEAKALRKLRH 600
Ac4       RAATHDVLAGLTAREAKVLRMRFGIDMNTDYTLEEVGKQFDVTRERIRQIEAKALRKLRH 598
Ac5       RAATHDVLAGLTAREAKVLRMRFGIDMNTDYTLEEVGKQFDVTRERIRQIEAKALRKLRH 600
          **********:**************.**********.***.***** ***********

Native    PSRSEVLRSFLDD 613
Ac1       PSRSEVLRSFLDD 107
Ac2       PSRSEVLRSFLDD 612
Ac3       PSRSDVLRSFLDD 613
Ac4       PSRPEVLRSFLDD 611
Ac5       PSRSEVLRSFLDD 613
          ***.:********
```

Fig. 3B Cont.

```
Native    MEQNPQSQLKLLVTRGKEQGYLTYAEVNDHLPEDIVDSDQIEDIIQMINDMGIQVMEEAP  60
pHBA1     ------------------------------------------------------------

Native    DADDLMLAENTADEDAAEAAAQVLSSVESEIGRTTDPVRMYMREMGTVELLTREGEIDIA  120
pHBA1     ------------------------------------------------------------

Native    KRIEDGINQVQCSVAEYPEAITYLLEQYDRVEAEEARLSDLITGFVDPNAEEDLAPTATH  180
pHBA1     ------------------------------------------------------------

Native    VGSELSQEDLDDDEDEDEEDGDDDSADDDNSIDPELAREKFAELRAQYVVTRDTIKAKGR  240
pHBA1     ------------------------------------------------------------

Native    SHATAQEEILKLSEVFKQFRLVPKQFDYLVNSMRVMMDRVRTQERLIMKLCVEQCKMPKK  300
pHBA1     ------------------------------------------------------------

Native    NFITLFTGNETSDTWFNAAIAMNKPWSEKLHDVSEEVHRALQKLQQIEEETGLTIEQVKD  360
pHBA1     ------------------------------------------------------------

Native    INRRMSIGEAKARRAKKEMVEANLRLVISIAKKYTNRGLQFLDLIQEGNIGLMKAVDKFE  420
pHBA1     ------------------------------------------------------------

Native    YRRGYKFSTYATWWIRQAITRSIADQARTIRIPVHMIETINKLNRISRQMLQEMGREPTP  480
pHBA1     ------------------------------------------------------------

Native    EELAERMLMPEDKIRKVLKIAKEPISMETPIGDDEDSHLGDFIEDTTLELPLDSATTESL  540
pHBA1     ------------------------------METPIGDDEDPHLGDFIEDTTLELPLVSATTVSL  34
                                        **********.*****************.****.**

Native    RAATHDVLAGLTAREAKVLRMRFGIDMNTDYTLEEVGKQFDVTRERIRQIEAKALRKLRH  600
pHBA1     RAATHDVLAGQTAREAKVLRMRFGVDMNTDYTLEEVGKQFDVTRVRIRQIEAKALRKLRH  94
          **********.************.*******************.***************

Native    PSRSEVLRSFLDD  613
pHBA1     PSRSEVLRSFLDD  107
          *************
```

GLOBAL TRANSCRIPTION MACHINERY ENGINEERING

RELATED APPLICATIONS

This application is a continuation of U.S. application Ser. No. 11/238,096, entitled "GLOBAL TRANSCRIPTION MACHINERY ENGINEERING," filed on Sep. 28, 2005, the entire disclosure of which is incorporated by reference herein in its entirety.

FIELD OF THE INVENTION

The invention relates to global transcription machinery engineering to produce altered cells having improved phenotypes.

BACKGROUND OF THE INVENTION

It is now generally accepted that many important cellular phenotypes, from disease states to metabolite overproduction, are affected by many genes. Yet, most cell and metabolic engineering approaches rely almost exclusively on the deletion or over-expression of single genes due to experimental limitations in vector construction and transformation efficiencies. These limitations preclude the simultaneous exploration of multiple gene modifications and confine gene modification searches to restricted sequential approaches where a single gene is modified at a time.

U.S. Pat. No. 5,686,283 described the use of a sigma factor encoded by rpoS to activate the expression of other bacterial genes that are latent or expressed at low levels in bacterial cells. This patent did not, however, describe mutating the sigma factor in order to change globally the transcription of genes.

U.S. Pat. No. 5,200,341 provides a mutated rpoH gene identified as a suppressor of a temperature sensitive rpoD gene by selection of temperature-resistant mutants of a bacterial strain having the temperature sensitive rpoD gene. No mutagenesis of the bacteria was undertaken, nor was the suppressor strain selected for a phenotype other than temperature resistance. When the mutant rpoH gene is added to other bacteria that are modified to express heterologous proteins, the heterologous proteins are accumulated at increased levels in the bacteria.

U.S. Pat. No. 6,156,532 describes microorganisms that are modified by introduction of a gene coding for a heat shock protein and a gene coding for a sigma factor (rpoH) that specifically functions for the heat shock protein gene to enhance expression amount of the heat shock protein in cells. The modified microorganisms are useful for producing fermentative products such as amino acids. The sigma factor used in the microorganisms was not mutated.

Directed evolution has been applied to microorganisms by shuffling of bacterial genomes for antibiotic (tylosin) production by *Streptomyces* (Zhang et al., *Nature*, 415, 644-646 (2002)) and acid tolerance of *Lactobacillus* (Patnaik et al., *Nature Biotech.* 20, 707-712 (2002)). These methods did not target mutations in any specific gene or genes, but instead non-recombinantly shuffled the genomes of strains having a desired phenotype using protoplast fusion, followed by selection of strains having improvements in the desired phenotype.

SUMMARY OF THE INVENTION

The invention utilizes global transcription machinery engineering to produce altered cells having improved phenotypes.

In particular, the invention is demonstrated through the generation of mutated bacterial sigma factors with varying preferences for promoters on a genome-wide level. The cells resulting from introduction of the mutated sigma factors have rapid and marked improvements in phenotypes, such as tolerance of deleterious culture conditions or improved production of metabolites.

The introduction of mutant transcription machinery into a cell, combined with methods and concepts of directed evolution, allows one to explore a vastly expanded search space in a high throughput manner by evaluating multiple, simultaneous gene alterations in order to improve complex cellular phenotypes.

Directed evolution through iterative rounds of mutagenesis and selection has been successful in broadening properties of antibodies and enzymes (W. P. Stemmer, *Nature* 370, 389-91 (1994)). These concepts have been recently extended and applied to non-coding, functional regions of DNA in the search for libraries of promoter activity spanning a broad dynamic range of strength as measured by different metrics (H. Alper, C. Fischer, E. Nevoigt, G. Stephanopoulos, *Proc Natl Acad Sci USA* 102, 12678-12683 (2005)). However, no evolution-inspired approaches have been directed towards the systematic modification of the global transcription machinery as a means of improving cellular phenotype. Yet, detailed biochemical studies suggest that both the transcription rate and in vitro preference for a given promoter sequence can be altered by modifying key residues on bacterial sigma factors (D. A. Siegele, J. C. Hu, W. A. Walter, C. A. Gross, *J Mol Biol* 206, 591-603 (1989); T. Gardella, H. Moyle, M. M. Susskind, *J Mol Biol* 206, 579-590 (1989)). Such modified transcription machinery units offer the unique opportunity to introduce simultaneous global transcription-level alterations that have the potential to impact cellular properties in a very profound way.

According to one aspect of the invention, methods for altering the phenotype of a cell are provided. The methods include mutating a nucleic acid encoding global transcription machinery and, optionally, its promoter, expressing the nucleic acid in a cell to provide an altered cell that includes mutated global transcription machinery, and culturing the altered cell. In some embodiments, the methods also include determining the phenotype of the altered cell or comparing the phenotype of the altered cell with the phenotype of the cell prior to alteration. In further embodiments, the methods also include repeating the mutation of the nucleic acid to produce a $n^{th}$ generation altered cell. In still other embodiments, the methods also include determining the phenotype of the $n^{th}$ generation altered cell or comparing the phenotype of the $n^{th}$ generation altered cell with the phenotype of any prior generation altered cell or of the cell prior to alteration. In preferred embodiments, the step of repeating the mutation of the global transcription machinery includes isolating a nucleic acid encoding the mutated global transcription machinery and optionally, its promoter, from the altered cell, mutating the nucleic acid, and introducing the mutated nucleic acid into another cell.

In certain embodiments, the cell is a prokaryotic cell, preferably a bacterial cell or an archaeal cell. In such embodiments, the global transcription machinery preferably is a sigma factor or an anti-sigma factor. Nucleic acid molecules encoding the sigma factors include rpoD ($\sigma^{70}$) genes, rpoF ($\sigma^{28}$) genes, rpoS ($\sigma^{38}$) genes, rpoH ($\sigma^{32}$) genes, rpoN ($\sigma^{54}$) genes, rpoE ($\sigma^{24}$) genes and fecI ($\sigma^{19}$) genes. The sigma factor or anti-sigma factor can be expressed from an expression vector.

In other embodiments, the cell is a eukaryotic cell. Preferred eukaryotic cells include yeast cells, mammalian cells, plant cells, insect cells, stem cells and fungus cells. In certain embodiments, one or more of the eukaryotic cells are contained in, or form, a multicellular organism. In some embodiments, the nucleic acid is expressed in the cell from a tissue-specific promoter, a cell-specific promoter, or an organelle-specific promoter.

In still other eukaryotic embodiments, the global transcription machinery binds to an RNA polymerase I, an RNA polymerase II or an RNA polymerase III, or a promoter of an RNA polymerase I, an RNA polymerase II or an RNA polymerase III. Preferred global transcription machinery includes TFIID or a subunit thereof, such as TATA-binding protein (TBP) or a TBP-associated factor (TAF). Nucleic acid molecules encoding the global transcription machinery include GAL11 genes, SIN4 genes, RGR1 genes, HRS1 genes, PAF1 genes, MED2 genes, SNF6 genes, SNF2 genes and SWI1 genes. The global transcription machinery, in other embodiments, is a nucleic acid methyltransferase, a histone methyltransferase, a histone acetylase or a histone deacetylase. The global transcription machinery is expressed from an expression vector in certain embodiments.

The nucleic acid in some embodiments is a nucleic acid of an organelle of the eukaryotic cell, preferably a mitochondrion or a chloroplast. The nucleic acid optionally is part of an expression vector.

The nucleic acid in certain embodiments is a member of a collection (e.g., a library) of nucleic acids. Thus the methods of the invention include, in some embodiments, introducing the collection into the cell.

In further embodiments, the step of expressing the nucleic acid includes integrating the nucleic acid into the genome or replacing a nucleic acid that encodes the endogenous global transcription machinery.

The mutation of the nucleic acid, in certain embodiments, includes directed evolution of the nucleic acid, such as mutation by error prone PCR or mutation by gene shuffling. In other embodiments, the mutation of the nucleic acid includes synthesizing the nucleic acid with one or more mutations.

Nucleic acid mutations in the invention can include one or more point mutations, and/or one or more truncations and/or deletions.

In some embodiments of the invention, a promoter binding region of the global transcription machinery is not disrupted or removed by the one or more truncations or deletions. In other embodiments, the mutated global transcription machinery exhibits increased transcription of genes relative to the unmutated global transcription machinery, decreased transcription of genes relative to the unmutated global transcription machinery, increased repression of gene transcription relative to the unmutated global transcription machinery, and/or decreased repression of gene transcription relative to the unmutated global transcription machinery.

In still other embodiments, the methods also include selecting the altered cell for a predetermined phenotype. Preferably, the step of selecting includes culturing the altered cell under selective conditions and/or high-throughput assays of individual cells for the phenotype.

A wide variety of phenotypes can be selected in accordance with the invention. In some preferred embodiments, the phenotype is increased tolerance of deleterious culture conditions. Such phenotypes include: solvent tolerance or hazardous waste tolerance, e.g., ethanol, hexane or cyclohexane; tolerance of industrial media; tolerance of high sugar concentration; tolerance of high salt concentration; tolerance of high temperatures; tolerance of extreme pH; tolerance of surfactants, and tolerance of a plurality of deleterious conditions.

In other preferred embodiments, the phenotype is increased metabolite production. Metabolites include lycopene, polyhydroxybutyrate (PHB), and therapeutic proteins, such as an antibody or an antibody fragment.

In still other preferred embodiments, the phenotype is tolerance to a toxic substrate, metabolic intermediate or product. Toxic metabolites include organic solvents, acetate, para-hydroxybenzoic acid (pHBA) and overexpressed proteins.

Additional phenotypes include antibiotic resistance and increased resistance to apoptosis.

In some embodiments, the cell is contained in a multicellular organism. In such embodiments, preferred phenotypes include one or more growth characteristics, generation time, resistance to one or more pests or diseases, production of fruit or other parts of a plant, one or more developmental changes, one or more lifespan alterations, gain or loss of function and/or increased robustness.

The cell used in the methods can be optimized for the phenotype prior to mutating the global transcription machinery.

The methods of the invention, in certain embodiments, also include identifying the changes in gene expression in the altered cell. The changes in gene expression preferably are determined using a nucleic acid microarray.

According to another aspect of the invention, methods for altering the phenotype of a cell are provided. The methods include altering the expression of one or more gene products in a first cell that are identified by detecting changes in gene expression in a second cell, wherein the changes in gene expression in the second cell are produced by mutating global transcription machinery of the second cell.

In some embodiments, altering the expression of the one or more gene products in the first cell includes increasing expression of one or more gene products that were increased in the second cell. In some preferred embodiments, the expression of the one or more gene products is increased by introducing into the first cell one or more expression vectors that express the one or more gene products, or by increasing the transcription of one or more endogenous genes that encode the one or more gene products. In the latter embodiments, increasing the transcription of the one or more endogenous genes includes mutating a transcriptional control (e.g., promoter/enhancer) sequence of the one or more genes.

In other embodiments, altering the expression of the one or more gene products in the first cell includes decreasing expression of one or more gene products that were decreased in the altered cell. Preferably, the expression of the one or more gene products is decreased by introducing into the first cell nucleic acid molecules that reduce the expression of the one or more gene products, such as nucleic acid molecules that are, or express, siRNA molecules. In other embodiments, the expression of the one or more gene products is decreased by mutating one or more genes that encode the one or more gene products or a transcriptional control (e.g., promoter/enhancer) sequence of the one or more genes.

The changes in gene expression in the second cell preferably are determined using a nucleic acid microarray.

In other embodiments, the changes in gene expression in the second cell are used to construct a model of a gene or protein network, and the model is used to select which of the one or more gene products in the network to alter.

The global transcription machinery in some embodiments includes more than one nucleic acid and/or polypeptide or is encoded by more than one nucleic acid.

Also provided according to the invention are cells produced by the foregoing methods.

According to another aspect of the invention, methods for altering the production of a metabolite are provided. The methods include mutating, according to any of the foregoing methods, global transcription machinery of a cell that produces a selected metabolite to produce an altered cell, and isolating altered cells that produce increased or decreased amounts of the selected metabolite. In some embodiments, the methods also include culturing the isolated cells, and recovering the metabolite from the cells or the cell culture. Preferred metabolites include lycopene, polyhydroxybutyrate (PHB) and therapeutic proteins, such as recombinant proteins, antibodies or antibody fragments.

In some embodiments the cells are prokaryotic cells, including bacterial cells or archaeal cells. In other embodiments, the cells are eukaryotic cells, including yeast cells, mammalian cells, plant cells, insect cells, stem cells and fungus cells. The global transcription machinery in certain of the latter embodiments is encoded by nucleic acid of an organelle of the eukaryotic cell, preferably a mitochondrion or a chloroplast.

According to another aspect of the invention, collections (e.g., a library) including a plurality of different nucleic acid molecule species are provided, in which it is preferred that each nucleic acid molecule species encodes global transcription machinery comprising different mutation(s). In some preferred embodiments, the global transcription machinery is a sigma factor or an anti-sigma factor. Preferably the nucleic acid encoding the sigma factor is a rpoD ($\sigma^{70}$) gene, a rpoF ($\sigma^{28}$) gene, a rpoS ($\sigma^{38}$) gene, a rpoH ($\sigma^{32}$) gene, a rpoN ($\sigma^{54}$) gene, a rpoE ($\sigma^{24}$) gene or a fecI ($\sigma^{19}$) gene. In other preferred embodiments, the global transcription machinery binds to an RNA polymerase I, an RNA polymerase II or an RNA polymerase III, or a promoter of an RNA polymerase I, an RNA polymerase II or an RNA polymerase III. Preferably the global transcription machinery is TFIID or a subunit thereof, such as a TATA-binding protein (TBP) or a TBP-associated factor (TAF). In other embodiments, the global transcription machinery is a nucleic acid methyltransferase, a histone methyltransferase, a histone acetylase or a histone deacetylase.

In certain embodiments, the nucleic acid molecule species are contained in expression vectors, preferably expressed from a tissue-specific promoter, a cell-specific promoter, or an organelle-specific promoter. The expression vectors preferably contain a plurality of different nucleic acid molecule species, wherein each nucleic acid molecule species encodes different global transcription machinery.

In other embodiments, the global transcription machinery is mutated by directed evolution, which preferably is performed using error prone PCR and/or using gene shuffling. Preferred mutation(s) in the global transcription machinery is/are one or more point mutations and/or one or more truncations and/or deletions. In some embodiments, the truncation does not include the promoter binding region of the global transcription machinery.

In still other embodiments, the global transcription machinery of a cell is mutated according to any of the foregoing methods.

In a further aspect of the invention, collections (e.g., a library) of cells is provide that includes the foregoing collections of nucleic acid molecules. In some embodiments, the collection includes a plurality of cells, each of the plurality of cells comprising one or more of the nucleic acid molecules. The cells preferably are prokaryotic cells, such as bacterial cells or archaeal cells or eukaryotic cells, such as yeast cells, mammalian cells, plant cells, insect cells, stem cells or fungus cells. In other embodiments, the nucleic acid molecules are integrated into the genome of the cells or replace nucleic acids that encode the endogenous global transcription machinery.

According to still another aspect of the invention, nucleic acids encoding global transcription machinery produced by a plurality of rounds of mutation are provided. The plurality of rounds of mutation preferably include directed evolution, such as that performed by mutation by error prone PCR and/or mutation by gene shuffling.

In some embodiments, the nucleic acid encodes a plurality of different global transcription machinery species. The nucleic acid preferably encodes a plurality of different versions of the same type of global transcription machinery species. Also provided according to the invention is global transcription machinery encoded by the foregoing nucleic acids.

In another aspect of the invention, truncated sigma factor proteins are provided that include (carboxy-terminal) region 4.

According to a further aspect of the invention, methods for bioremediation of a selected waste product are provided. The methods include mutating, according to any of the foregoing methods, global transcription machinery of a cell to produce an altered cell, isolating altered cells that metabolize an increased amount of the selected waste product relative to unaltered cells, culturing the isolated cells, and exposing the altered cells to the selected waste product, thereby providing bioremediation of the selected waste product.

These and other aspects of the invention, as well as various embodiments thereof, will become more apparent in reference to the drawings and detailed description of the invention.

BRIEF DESCRIPTION OF THE DRAWINGS

FIGS. 2A-2D show the isolation of ethanol tolerant sigma factor mutants. Strains were isolated containing mutant sigma factors which increased the tolerance to ethanol. FIG. 2A: The overall enhancement of phenotype through the various round of directed evolution of the mutant factor. Overall enhancement (y-axis) is assessed by taking the summation of the fold reduction of doubling time for the mutant over the control at 0, 20, 40, 50, 60, 70 and 80 g/L of ethanol. By the third round, the improvement in growth rate seems to be small and incremental. FIG. 2B: The location of mutations on the $\sigma^{70}$ protein are indicated in relation to previously identified critical functional regions. The second round mutagenesis resulted in the identification of a truncated factor containing only one of the two prior mutations in that region. FIG. 2C: Growth curves are presented for the Round 3 mutant (Red) and control (Blue) strains. The round 3 mutant has significantly improved growth rates at all tested ethanol concentrations. FIG. 2D: Amino acid sequence alignments of the ethanol tolerant mutant sigma factors (Native, SEQ ID NO:17; Round 1, SEQ ID NO:18; Round 2, SEQ ID NO:19; Round 3, SEQ ID NO:20).

FIGS. 3A-3C show sequence analysis of sigma factors for additional phenotypes. FIG. 3A: The location of the mutations in the acetate and pHBA mutants of the $\sigma^{70}$ protein area indicated in relation to previously identified critical functional regions. The vast majority of the acetate mutants were full-length sigma factors. The identified mutant for pHBA was a truncated factor which is expected to act as an inhibitor to specific gene transcription. FIG. 3B: Amino acid sequence alignments of the acetate tolerant mutant sigma factors (Native, SEQ ID NO:17; Act, SEQ ID NO:21; Ac2, SEQ ID NO:22; Ac3, SEQ ID NO:23; Ac4, SEQ ID NO:24; Ac5, SEQ ID NO:25). FIG. 3C: Amino acid sequence alignments of the pHBA tolerant mutant sigma factors (Native, SEQ ID NO:17; pHBA1, SEQ ID NO:26).

FIG. 4 also shows the sequences of the best hexane-tolerant mutants, Hex-12 and Hex-18.

FIG. 10A presents the results for various strains (bars in red and yellow represent controls) obtained using sigma factor engineering. FIG. 10B presents the results of selected strains from a random knockout library created using transposon mutagenesis.

DETAILED DESCRIPTION OF THE INVENTION

Figure 1:
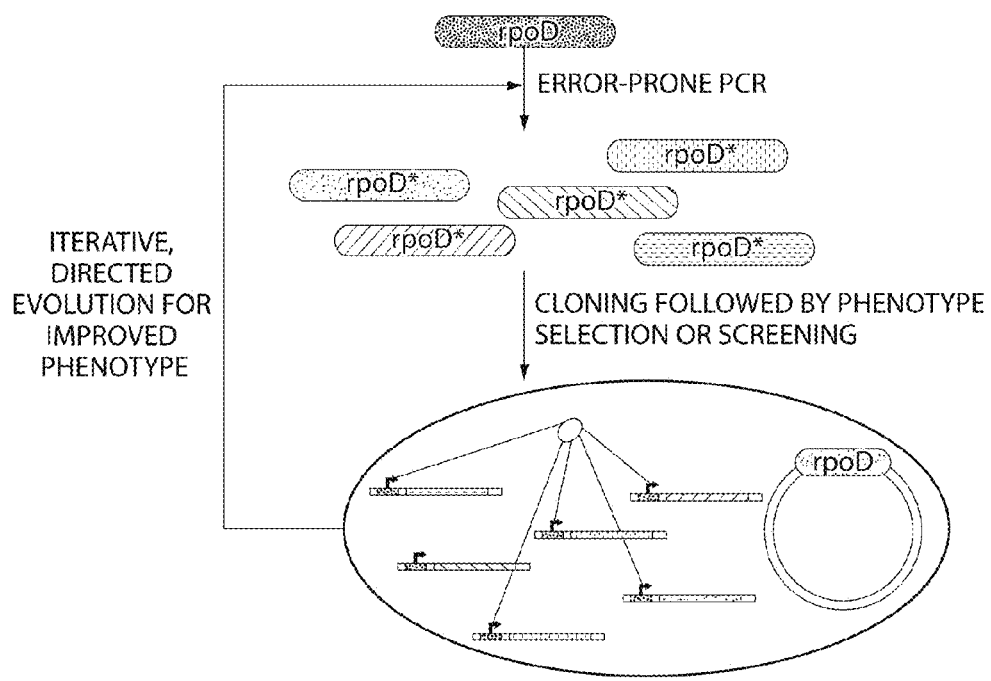
FIG. 1 depicts the basic methodology of global transcription machinery engineering. By introducing altered global transcription machinery into a cell, the transcriptome is altered and the expression level of genes changes in a global manner. In this study, the bacterial sigma factor 70 (encoded by rpoD) was subjected to error-prone PCR to generate various mutants. The mutants were then cloned into a low-copy expression vector, during which the possibility arose for a truncated form of the sigma factor due to the presence of a nearly complete internal restriction enzyme site. The vectors were then transformed into E. coli and screened based on the desired phenotype. Isolated mutants can then be subjected to subsequent rounds of mutagenesis and selection to further improve phenotypes.

Global transcription machinery is responsible for controlling the transcriptome in all cellular systems (prokaryotic and eukaryotic). In bacterial systems, the sigma factors play a critical role in orchestrating global transcription by focusing the promoter preferences of the RNA polymerase holoenzyme (R. R. Burgess, L. Anthony, Curr. Opin. Microbiol 4, 126-131 (2001)). Escherichia coli contains six alternative sigma factors and one principal factor, $\sigma^{70}$, encoded by the gene rpoD. On the protein level, regions of residues have been analyzed for contacts with promoter sites and the holoenzyme (J. T. Owens et al., PNAS 95, 6021-6026 (1998)). Crystal structure analysis and site specific mutagenesis of $\sigma^{70}$ in E. coli and other bacteria, have demonstrated the ability to alter the in vitro promoter preference of the RNA polymerase holoenzyme evidenced by increased or decreased transcription of a reporter gene (A. Malhotra, E. Severinova, S. A. Darst, Cell 87, 127-36 (1996)). This invention exploits the ability to generate mutant sigma factors with varying preferences for promoters on a genome-wide level.

Traditional strain improvement paradigms rely predominantly on making sequential, single-gene modifications and often fail to reach the global maxima. The reason is that metabolic landscapes are complex (H. Alper, K. Miyaoku, G. Stephanopoulos, Nat Biotechnol 23, 612-616 (2005); H. Alper, Y.-S. Jin, J. F. Moxley, G. Stephanopoulos, Metab Eng 7, 155-164 (2005)) and incremental or greedy search algorithms fail to uncover synthetic mutants that are beneficial only when all mutations are simultaneously introduced. Protein engineering on the other hand can quickly improve fitness, through randomized mutagenesis and selection for enhanced antibody affinity, enzyme specificity, or catalytic activity (E. T. Boder, K. S. Midelfort, K. D. Wittrup, Proc Natl Acad Sci USA 97, 10701-5 (2000); A. Glieder, E. T. Farinas, F. H. Arnold, Nat Biotechnol 20, 1135-9 (2002); N. Varadarajan, J. Gam, M. J. Olsen, G. Georgiou, B. L. Iverson, Proc Natl Acad Sci USA 102, 6855-60 (2005)). An important reason for the drastic enhancement obtained in these examples is the ability of these methods to probe a significant subset of the huge amino acid combinatorial space by evaluating many simultaneous mutations. Using the invention, we exploit the global regulatory functions of the $\sigma^{70}$ sigma factor to similarly introduce multiple simultaneous gene expression changes and thus facilitate whole-cell engineering by selecting mutants responsible for improved cellular phenotype.

The invention provides methods for altering the phenotype of a cell. In the methods include mutating a nucleic acid encoding a global transcription machinery protein and, optionally, its promoter, expressing the nucleic acid in a cell to provide an altered cell that includes a mutated global transcription machinery protein, and culturing the altered cell. As used herein, "global transcription machinery" is one or more molecules that modulates the transcription of a plurality of genes. The global transcription machinery can be proteins that affect gene transcription by interacting with and modulating the activity of a RNA polymerase molecule. The global transcription machinery also can be proteins that alter the ability of the genome of a cell to be transcribed (e.g., methyltransferases, histone methyltransferases, histone acetylases and deacetylases). Further, global transcription machinery can be molecules other than proteins (e.g., micro RNAs) that alter transcription of a plurality of genes.

Global transcription machinery useful in accordance with the invention include bacterial sigma factors and anti-sigma factors. Exemplary genes that encode sigma factors include rpoD, encoding $\sigma^{70}$; rpoF, encoding $\sigma^{28}$; rpoS, encoding $\sigma^{38}$; rpoH, encoding $\sigma^{32}$; rpoN, encoding $\sigma^{54}$; rpoE, encoding $\sigma^{24}$; and fecI, encoding $\sigma^{19}$. Anti-sigma factors bind to the sigma factors and control their availability and consequently transcription. In E. coli, anti-sigma factors are encoded by rsd (for sigma factor 70) or flgM, among others. The anti-sigma factors can be mutated to control their impact in transcription for normal cells. In addition, novel pairings of mutant sigma factors with mutant anti-sigma factors can be created to create further control of transcription in cells. For example, the anti-sigma factor can be expressed using an inducible promoter, which allows for tunable control of the phenotype imparted by the mutant sigma factor.

Global transcription machinery also includes polypeptides that bind to and modulate the activity of eukaryotic RNA polymerases, such as RNA polymerase I, RNA polymerase II or RNA polymerase III, or a promoter of RNA polymerase I, RNA polymerase II or RNA polymerase III. Examples of such eukaryotic global transcription machinery are TFIID or a subunit thereof, such as TATA-binding protein (TBP) or a TBP-associated factor (TAF), and elongation factors. Further examples from yeast include GAL11, SIN4, RGR1, HRS1, PAF1, MED2, SNF6, SNF2, and SWI1.

Global transcription machinery also includes polypeptides that alter the ability of chromosomal DNA to be transcribed, such as nucleic acid methyltransferases (e.g., DamMT, DNMT1, Dnmt3a); histone methyltransferases (e.g., Set1, MLL1); histone acetylases (e.g., PCAF, GCN5, Sas2p and other MYST-type histone acetylases, TIP60); and histone deacetylases (e.g., HDAC1, HDA1, HDAC2, HDAC3, RPD3, HDAC8, Sir2p), as well as associated factors (e.g., HDACs are associated with mSin3A, Mi-2/NRD, CoREST/kiaa0071, N-CoR and SMRT).

Still other global transcription machinery is encoded by nucleic acid molecules of an organelle of a eukaryotic cell, such as a mitochondrion or a chloroplast.

In many instances, the process of mutating the global transcription machinery will include iteratively making a plurality of mutations of the global transcription machinery, but it need not, as even a single mutation of the global transcription machinery can result in dramatic alteration of phenotype, as is demonstrated herein.

While the methods of the invention typically are carried out by mutating the global transcription machinery followed by introducing the mutated global transcription machinery into a cell to create an altered cell, it is also possible to mutate endogenous global transcription machinery genes, e.g., by replacement with mutant global transcription machinery or by in situ mutation of the endogenous global transcription machinery. As used herein, "endogenous" means native to the cell; in the case of mutating global transcription machinery, endogenous refers to the gene or genes of the global transcription machinery that are in the cell. In contrast, the more typical methodology includes mutation of a global transcription machinery gene or genes outside of the cell, followed by introduction of the mutated gene(s) into the cell.

The global transcription machinery genes can be of the same species or different species as the cell into which they are introduced. For example, as shown herein, $E.$ $coli$ sigma factor 70 was mutated and introduced into $E.$ $coli$ to alter the phenotype of the $E$ $coli$ cells. Other global transcription machinery of $E.$ $coli$ also could be used in the same fashion. Similarly, global transcription machinery of a particular yeast species, e.g., $S.$ $cerevisiae$ or $S.$ $pombe$, could be mutated and introduced into the same yeast species. Likewise, global transcription machinery of a nematode species, e.g., $C.$ $elegans$, or a mammalian species, e.g., $M.$ $musculus$, $R.$ $norvegicus$ or $H.$ $sapiens$, can be mutated and introduced into the same species in a manner similar to the specific examples provided herein, using standard recombinant genetic techniques.

Alternatively, global transcription machinery from different species can be utilized to provide additional variation in the transcriptional control of genes. For example, global transcription machinery of a $Streptomyces$ bacterium could be mutated and introduced into $E.$ $coli$. The different global transcription machinery also could be sourced from different kingdoms or phyla of organisms. Depending on the method of mutation used, same and different global transcription machinery can be combined for use in the methods of the invention, e.g., by gene shuffling.

Optionally, the transcriptional control sequences of global transcription machinery can be mutated, rather than the coding sequence itself. Transcriptional control sequences include promoter and enhancer sequences. The mutated promoter and/or enhancer sequences, linked to the global transcription machinery coding sequence, can then be introduced into the cell.

After the mutant global transcription machinery is introduced into the cell to make an altered cell, then the phenotype of the altered cell is determined/assayed. This can be done by selecting altered cells for the presence (or absence) of a particular phenotype. Examples of phenotypes are described in greater detail below. The phenotype also can be determined by comparing the phenotype of the altered cell with the phenotype of the cell prior to alteration.

In preferred embodiments, the mutation of the global transcription machinery and introduction of the mutated global transcription machinery are repeated one or more times to produce an "$n^{th}$ generation" altered cell, where "n" is the number of iterations of the mutation and introduction of the global transcription machinery. For example, repeating the mutation and introduction of the global transcription machinery once (after the initial mutation and introduction of the global transcription machinery) results in a second generation altered cell. The next iteration results in a third generation altered cell, and so on. The phenotypes of the cells containing iteratively mutated global transcription machinery then are determined (or compared with a cell containing non-mutated global transcription machinery or a previous iteration of the mutant global transcription machinery) as described elsewhere herein.

The process of iteratively mutating the global transcription machinery allows for improvement of phenotype over sequential mutation steps, each of which may result in multiple mutations of the global transcription machinery. It is also possible that the iterative mutation may result in mutations of particular amino acid residues "appearing" and "disappearing" in the global transcription machinery over the iterative process. Examples of such mutations are provided in the working examples.

In a typical use of the methodology, the global transcription machinery is subjected to directed evolution by mutating a nucleic acid molecule that encodes the global transcription machinery. A preferred method to mutate the nucleic acid molecule is to subject the coding sequence to mutagenesis, and then to insert the nucleic acid molecule into a vector (e.g., a plasmid). This process may be inverted if desired, i.e., first insert the nucleic acid molecule into a vector, and then subject the sequence to mutagenesis, although it is preferred to mutate the coding sequence prior to inserting it in a vector.

When the directed evolution of the global transcription machinery is repeated, i.e., in the iterative processes of the invention, a preferred method includes the isolation of a nucleic acid encoding the mutated global transcription machinery and optionally, its promoter, from the altered cell. The isolated nucleic acid molecule is then mutated (producing a nucleic acid encoding a second generation mutated global transcription machinery), and subsequently introduced into another cell.

The isolated nucleic acid molecule when mutated, forms a collection of mutated nucleic acid molecules that have different mutations or sets of mutations. For example, the nucleic acid molecule when mutated randomly can have set of mutations that includes mutations at one or more positions along the length of the nucleic acid molecule. Thus, a first member of the set may have one mutation at nucleotide n1 (wherein nx represents a number of the nucleotide sequence of the nucleic acid molecule, with x being the position of the nucleotide from the first to the last nucleotide of the molecule). A second member of the set may have one mutation at nucleotide n2. A third member of the set may have two mutations at nucleotides n1 and n3. A fourth member of the set may have two mutations at positions n4 and n5. A fifth member of the set may have three mutations: two point mutations at nucleotides n4 and n5, and a deletion of nucleotides n6-n7. A sixth member of the set may have point mutations at nucleotides n1, n5 and n8, and a truncation of the 3' terminal nucleotides. A seventh member of the set may have nucleotides n9-n10 switched with nucleotides n11-n12. Various other combinations can be readily envisioned by one of ordinary skill in the art, including combinations of random and directed mutations.

The collection of nucleic acid molecules can be a library of nucleic acids, such as a number of different mutated nucleic acid molecules inserted in a vector. Such a library can be stored, replicated, aliquoted and/or introduced into cells to produce altered cells in accordance with standard methods of molecular biology.

Mutation of the global transcription machinery for directed evolution preferably is random. However, it also is possible to limit the randomness of the mutations introduced into the global transcription machinery, to make a non-random or partially random mutation to the global transcription machinery, or some combination of these mutations. For example, for a partially random mutation, the mutation(s) may be confined to a certain portion of the nucleic acid molecule encoding the global transcription machinery.

The method of mutation can be selected based on the type of mutations that are desired. For example, for random mutations, methods such as error-prone PCR amplification of the nucleic acid molecule can be used. Site-directed mutagenesis can be used to introduce specific mutations at specific nucleotides of the nucleic acid molecule. Synthesis of the nucleic acid molecules can be used to introduce specific mutations and/or random mutations, the latter at one or more specific nucleotides, or across the entire length of the nucleic acid molecule. Methods for synthesis of nucleic acids are well known in the art (e.g., Tian et al., Nature 432: 1050-1053 (2004)).

DNA shuffling (also known as gene shuffling) can be used to introduce still other mutations by switching segments of nucleic acid molecules. See, e.g., U.S. Pat. No. 6,518,065, related patents, and references cited therein. The nucleic acid molecules used as the source material to be shuffled can be nucleic acid molecule(s) that encode(s) a single type of global transcription machinery (e.g., $\sigma^{70}$), or more than one type of global transcription machinery. For example, nucleic acid molecules encoding different global transcription machinery, such as different sigma factors of a single species (e.g., $\sigma^{70}$ and $\sigma^{28}$ of E. coli), or sigma factors from different species can be shuffled. Likewise, nucleic acid molecules encoding different types of global transcription machinery, e.g., sigma factor 70 and TFIID, can be shuffled.

A variety of other methods of mutating nucleic acid molecules, in a random or non-random fashion, are well known to one of ordinary skill in the art. One or more different methods can be used combinatorially to make mutations in nucleic acid molecules encoding global transcription machinery. In this aspect, "combinatorially" means that different types of mutations are combined in a single nucleic acid molecule, and assorted in a set of nucleic acid molecules. Different types of mutations include point mutations, truncations of nucleotides, deletions of nucleotides, additions of nucleotides, substitutions of nucleotides, and shuffling (e.g., re-assortment) of segments of nucleotides. Thus, any single nucleic acid molecule can have one or more types of mutations, and these can be randomly or non-randomly assorted in a set of nucleic acid molecules. For example, a set of nucleic acid molecules can have a mutation common to each nucleic acid molecule in the set, and a variable number of mutations that are not common to each nucleic acid molecule in the set. The common mutation, for example, may be one that is found to be advantageous to a desired altered phenotype of the cell.

Preferably a promoter binding region of the global transcription machinery is not disrupted or removed by the one or more truncations or deletions.

The mutated global transcription machinery can exhibit increased or decreased transcription of genes relative to the unmutated global transcription machinery. In addition, the mutated global transcription machinery can exhibit increased or decreased repression of transcription of genes relative to the unmutated global transcription machinery.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to: plasmids, phagemids, virus genomes and artificial chromosomes.

A cloning vector is one which is able to replicate autonomously or integrated in the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding a CT antigen polypeptide or fragment or variant thereof. That heterologous DNA (RNA) is placed under operable control of transcriptional elements to permit the expression of the heterologous DNA in the host cell.

Preferred systems for mRNA expression in mammalian cells are those such as pRc/CMV or pcDNA3.1 (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr Virus (EBV) origin of replication, facilitating the maintenance of plasmid as a multicopy extrachromosomal element.

When the nucleic acid molecule that encodes mutated global transcription machinery is expressed in a cell, a variety of transcription control sequences (e.g., promoter/enhancer sequences) can be used to direct expression of the global transcription machinery. The promoter can be a native promoter, i.e., the promoter of the global transcription machinery gene, which provides normal regulation of expression of the global transcription machinery. The promoter also can be one that is ubiquitously expressed, such as beta-actin, ubiquitin B, phage promoters or the cytomegalovirus promoter. A promoter useful in the invention also can be one that does not ubiquitously express the global transcription machinery. For example, the global transcription machinery can be expressed in a cell using a tissue-specific promoter, a cell-specific promoter, or an organelle-specific promoter. A variety of conditional promoters also can be used, such as promoters controlled by the presence or absence of a molecule, such as the tetracycline-responsive promoter (M. Gossen and H. Bujard, *Proc. Natl. Acad. Sci. USA*, 89, 5547-5551 (1992)).

A nucleic acid molecule that encodes mutated global transcription machinery can be introduced into a cell or cells using methods and techniques that are standard in the art. For example, nucleic acid molecules can be introduced by various transfection methods, transduction, electroporation, particle bombardment, injection (including microinjection of cells and injection into multicellular organisms), lipofection, yeast spheroplast/cell fusion for YACs (yeast artificial chromosomes), *Agrobacterium*-mediated transformation for plant cells, etc.

Expressing the nucleic acid molecule encoding mutated global transcription machinery also may be accomplished by integrating the nucleic acid molecule into the genome or by replacing a nucleic acid sequence that encodes the endogenous global transcription machinery.

By mutating global transcription machinery, novel compositions are provided, including nucleic acid molecules encoding global transcription machinery produced by a plurality of rounds of mutation. The plurality of rounds of mutation can include directed evolution, in which each round of mutation is followed by a selection process to select the mutated global transcription machinery that confer a desired phenotype. The methods of mutation and selection of the mutated global transcription machinery are as described elsewhere herein. Global transcription machinery produced by these nucleic acid molecules also are provided.

In certain cases, it has been found that mutated global transcription machinery are truncated forms of the unmutated global transcription machinery. In particular, for sigma factor 70, it has been found that an amino-terminal truncation of $\sigma^{70}$ that leaves only the carboxyl-terminus of the $\sigma^{70}$ protein confers advantageous phenotypes to bacteria in which it is introduced. Thus, fragments of global transcription machinery are provided, particularly fragments that retain the promoter binding properties of the unmutated global transcription machinery, more particularly $\sigma^{70}$ fragments that include region 4. Nucleic acid molecules encoding the truncated global transcription machinery also are provided, including nucleic acid molecules as contained in vectors and/or cells.

The cells useful in the invention include prokaryotic cells and eukaryotic cells. Prokaryotic cells include bacterial cells and archaeal cells. Eukaryotic cells include yeast cells, mammalian cells, plant cells, insect cells, stem cells, and fungus cells. Eukaryotic cells may be contained in, e.g., part of or all of, a multicellular organism. Multicellular organisms include mammals, nematodes such as *Caenorhabditis elegans*, plants such as *Arabidopsis thaliana, Bombyx mori, Xenopus laevis*, zebrafish (*Danio rerio*), sea urchin and *Drosophila melanogaster*.

Examples of bacteria include *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp. and *Pantoea* spp.

Examples of archaea (also known as archaebacteria) include *Methylomonas* spp., *Sulfolobus* spp., *Methylobacterium* spp. *Halobacterium* spp., *Methanobacterium* spp., *Methanococci* spp., *Methanopyri* spp., *Archaeoglobus* spp., *Ferroglobus* spp., *Thermoplasmata* spp. and *Thermococci* spp.

Examples of yeast include *Saccharomyces* spp., *Schizosaccharomyces* spp., *Pichia* spp., *Paffia* spp., *Kluyveromyces* spp., *Candida* spp., *Talaromyces* spp., and *Debaryomyces* spp.

Examples of fungi include *Aspergillus* spp., *Pennicilium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., and *Trichoderma* spp.

Examples of insect cells include *Spodoptera frugiperda* cell lines such as Sf9 and Sf21, *Drosophila melanogaster* cell lines such as Kc, Ca, 311, DH14, DH15, DH33P1, P2, P4 and SCHNEIDER-2 (D. Me1-S2) and *Lymantria dispar* cedll lines such as 652Y.

Examples of mammalian cells include primary cells, such as stem cells and dendritic cells, and mammalian cell lines such as Vero, HEK 293, Sp2/0, P3UI, CHO, COS, HeLa, BAE-1, MRC-5, NIH3T3, L929, HEPG2, NS0, U937, HL60, YAC1, BHK, ROS, Y79, Neuro2a, NRK, MCF-10, RAW 264.7, and TBY-2.

Stem cell lines include hESC BG01, hESC BG01V, ES-057BL/6, ES-D3 GL, J1, R1, RW.4, 7AC5/EYFP, and R1/E. Additional human stem cell lines include (NIH designations) CH01, CH02, GE01, GE07, GE09, GE13, GE14, GE91, GE92, SA19, MB01, MB02, MB03, NC01, NC02, NC03, RL05, RL07, RL10, RL13, RL15, RL20, and RL21.

Directed evolution of global transcription machinery produces altered cells, some of which have altered phenotypes. Thus the invention also includes selecting altered cells for a predetermined phenotype or phenotypes. Selecting for a predetermined phenotype can be accomplished by culturing the altered cells under selective conditions. Selecting for a predetermined phenotype also can be accomplished by high-throughput assays of individual cells for the phenotype. For example, cells can be selected for tolerance to deleterious conditions and/or for increased production of metabolites. Tolerance phenotypes include tolerance of solvents such as ethanol, and organic solvents such as hexane or cyclohexane; tolerance of toxic metabolites such as acetate, para-hydroxybenzoic acid (pHBA), para-hydroxycinnamic acid, hydroxypropionaldehyde, overexpressed proteins, organic solvents and immuno-suppressant molecules; tolerance of surfactants; tolerance of high sugar concentrations; tolerance of high temperatures; tolerance of extreme pH conditions (high or low); resistance to apoptosis; tolerance of toxic substrates such as hazardous waste; tolerance of industrial media; increased antibiotic resistance, etc. Selection for ethanol tolerance, organic solvent tolerance, acetate tolerance, para-hydroxybenzoic acid tolerance, SDS tolerance and antibiotic resistance are exemplified in the working examples. In other working examples, selection for increased production of lycopene and polyhydroxybutyrate are exemplified.

Additional phenotypes that are manifested in multicellular organisms also can be selected. Mutant versions of global transcription machinery can be introduced into mammalian or other eukaryotic cell lines, or even introduced into whole organism (e.g., through introduction into germ cells lines or injections into oocytes) to allow for a screening of phenotypes. Such phenotypes may or may not be manifested in a single cell of the organism, and include: one or more growth characteristics, generation time, resistance to one or more pests or diseases, production of fruit or other parts of a plant, one or more developmental changes, one or more lifespan alterations, gain or loss of function, increased robustness, etc.

As used herein with respect to altered cells containing mutated global transcription machinery, "tolerance" means that an altered cell is able to withstand the deleterious conditions to a greater extent than an unaltered cell, or a previously altered cell. For example, the unaltered or previously altered cell is a "parent" of the "child" altered cell, or the unaltered or previously altered cell is the $(n-1)^{th}$ generation as compared to the cell being tested, which is $n^{th}$ generation. "Withstanding the deleterious conditions" means that the altered cell has increased growth and/or survival relative to the unaltered or previously altered cell. This concept also includes increased production of metabolites that are toxic to cells.

With respect to tolerance of high sugar concentrations, such concentrations can be $\geq 100$ g/L, $\geq 120$ g/L, $\geq 140$ g/L, $\geq 160$ g/L, $\geq 180$ g/L, $\geq 200$ g/L, etc. With respect to tolerance of high salt concentrations, such concentrations can be $\geq 1$ M, $\geq 2$ M, $\geq 3$ M, $\geq 4$ M, $\geq 5$ M, etc. With respect to tolerance of high temperatures, the temperatures can be, e.g., $\geq 42°$ C., $\geq 44°$ C., $\geq 46°$ C., $\geq 48°$ C., $\geq 50°$ C. for bacterial cells. Other temperature cutoffs may be selected according to the cell type used. With respect to tolerance of extreme pH, exemplary pH cutoffs are, e.g., $\geq$pH10, $\geq$pH11, $\geq$pH12, $\geq$pH13, or $\leq$pH4.0, $\leq$pH3.0, $\leq$pH2.0, $\leq$pH1.0. With respect to tolerance of surfactants, exemplary surfactant concentrations are $\geq 5\%$ w/v, $\geq 6\%$ w/v, $\geq 7\%$ w/v, $\geq 8\%$ w/v, $\geq 9\%$ w/v, $\geq 10\%$ w/v, $\geq 12\%$ w/v, $\geq 15\%$ w/v, etc.

The invention includes obtaining increased production of metabolites by cells. As used herein, a "metabolite" is any molecule that is made or can be made in a cell. Metabolites include metabolic intermediates or end products, any of which may be toxic to the cell, in which case the increased production may involve tolerance of the toxic metabolite. Thus metabolites include small molecules, peptides, large proteins, lipids, sugars, etc. Exemplary metabolites include the metabolites demonstrated in the working examples (lycopene and polyhydroxybutyrate); therapeutic proteins, such as antibodies or antibody fragments.

The invention also provides for selecting for a plurality of phenotypes, such as tolerance of a plurality of deleterious conditions, increased production of a plurality of metabolites, or a combination of these.

It may be advantageous to use cells that are previously optimized for the predetermined phenotype prior to introducing mutated global transcription machinery. Thus, in the production of lycopene, for example, rather than starting with a bacterial cell that produces only a small amount of lycopene, one preferentially uses a cell that produces a higher amount of lycopene, more preferably an optimized amount of lycopene. In such cases, the mutated global transcription machinery is used to further improve an already-improved phenotype.

Via the actions of the mutated global transcription machinery, the altered cells will have altered expression of genes. The methods of the invention can, in certain aspects, include identifying the changes in gene expression in the altered cell. Changes in gene expression can be identified using a variety of methods well known in the art. Preferably the changes in gene expression are determined using a nucleic acid microarray.

In some aspects of the invention, one or more of the changes in gene expression that are produced in a cell by mutated global transcription machinery can be reproduced in another cell in order to produce the same (or a similar) phenotype. The changes in gene expression produced by the mutated global transcription machinery can be identified as described above. Individual gene(s) can then be targeted for modulation, through recombinant gene expression or other means. For example, mutated global transcription machinery may produce increases in the expression of genes A, B, C, D, and E, and decreases in the expression of genes F, G, and H. The invention includes modulating the expression of one or more of these genes in order to reproduce the phenotype that is produced by the mutated global transcription machinery. To reproduce the predetermined phenotype, one or more of genes A, B, C, D, E, F, G, and H can be increased, e.g., by introducing into the cell expression vector(s) containing the gene sequence(s), increasing the transcription of one or more endogenous genes that encode the one or more gene products, or by mutating a transcriptional control (e.g., promoter/enhancer) sequence of the one or more genes, or decreased, e.g., by introducing into the first cell nucleic acid molecules that reduce the expression of the one or more gene products such as nucleic acid molecules are, or express, siRNA molecules, or by mutating one or more genes that encode the one or more gene products or a transcriptional control (e.g., promoter/enhancer) sequence of the one or more genes.

Optionally, the changes in gene expression in the cell containing the mutated global transcription machinery are used to construct a model of a gene or protein network, which then is used to select which of the one or more gene products in the network to alter. Models of gene or protein networks can be produced via the methods of Ideker and colleagues (see, e.g., Kelley et al., *Proc Natl Acad Sci USA* 100(20), 11394-11399 (2003); Yeang et al. *Genome Biology* 6(7), Article R62 (2005); Ideker et al., *Bioinformatics*. 18 Suppl 1:S233-40 (2002)) or Liao and colleagues (see, e.g., Liao et al., *Proc Natl Acad Sci USA* 100(26), 15522-15527 (2003); Yang et al., *BMC Genomics* 6, 90 (2005)), The invention also includes cells produced by any of the methods described herein, and multicellular organisms that contain such cells. The cells are useful for a variety of purposes, including: industrial production of molecules (e.g., many of the tolerance phenotypes and increased metabolite production phenotypes); bioremediation (e.g., hazardous waste tolerance phenotypes); identification of genes active in cancer causation (e.g., apoptosis resistance phenotypes); identification of genes active in resistance of bacteria and other prokaryotes to antibiotics; identification of genes active in resistance of pests to pesticides; etc.

In another aspect, the invention provides methods for altering the production of a metabolite. The methods include mutating global transcription machinery to produce an altered cell, in accordance with the methods described elsewhere herein. The cell preferably is a cell that produces a selected metabolite, and as described above, preferably is previously optimized for production of the metabolite. Altered cells that produce increased or decreased amounts of the selected metabolite can then be isolated. The methods also can include culturing the isolated cells and recovering the metabolite from the cells or the cell culture. The steps of culturing cells and recovering metabolite can be carried out using methods well known in the art. Various preferred cell types, global transcription machinery and metabolites are provided elsewhere herein.

Another method provided in accordance with the invention is a method for bioremediation of a selected waste product. "Bioremediation", as used herein, is the use of microbes, such as bacteria and other prokaryotes, to enhance the elimination of toxic compounds in the environment. One of the difficulties in bioremediation is obtaining a bacterial strain or other microbe that effectively remediates a site, based on the particular toxins present at that site. The methods for altering the phenotype of cells described herein represents and ideal way to provide such bacterial strains. As one example, bioremediation can be accomplished by mutating global transcription machinery of a cell to produce an altered cell in accordance with the invention and isolating altered cells that metabolize an increased amount of the selected waste product relative to unaltered cells. The isolated altered cells then can be cultured, and exposed to the selected waste product, thereby providing bioremediation of the selected waste product. As an alternative, a sample of the materials in the toxic waste site needing remediation could serve as the selection medium, thereby obtaining microbes specifically selected for the particular mixture of toxins present at the particular toxic waste site.

The invention also provides collections of nucleic acid molecules, which may be understood in the art as a "library" of nucleic acid molecules using the standard nomenclature of molecular biology. Such collections/libraries include a plurality of different nucleic acid molecule species, with each nucleic acid molecule species encoding global transcription machinery that has different mutation(s) as described elsewhere herein.

Other collections/libraries of the invention are collections/libraries of cells that include the collections/libraries of nucleic acid molecules described above. The collections/libraries include a plurality of cells, with each cell of the plurality of cells including one or more of the nucleic acid molecules. The cell types present in the collection are as described elsewhere herein, and include single cells as well as multicellular organisms that include one or more of such cells. In the libraries of cells, the nucleic acid molecules can exist as extrachromosomal nucleic acids (e.g., on a plasmid), can be integrated into the genome of the cells, and can replace nucleic acids that encode the endogenous global transcription machinery.

The collections/libraries of nucleic acids or cells can be provided to a user for a number of uses. For example, a collection of cells can be screened for a phenotype desired by the user. Likewise, a collection of nucleic acid molecules can be introduced into a cell by the user to make altered cells, and then the altered cells can be screened for a particular phenotype(s) of interest. For example, to use a phenotype described herein, a user seeking to increase lycopene production and possessing a bacterial strain that produces a certain amount of lycopene could introduce a collection of mutated global transcriptions factor(s) into the bacterial strain, and then screen for improved production of lycopene. Subsequent rounds of directed evolution by mutation and reintroduction of the global transcription machinery also can be carried out to obtain further improvements in lycopene production.

Collections/libraries can be stored in containers that are commonly used in the art, such as tubes, microwell plates, etc.

EXAMPLES

Materials and Methods
Strains and Media

*E. coli* DH5α (Invitrogen, Carlsbad, Calif.) was used for routine transformations as described in the protocol as well as for all phenotype analysis in this experiment. Strains were grown at 37° C. with 225 RPM orbital shaking in either LB-Miller medium or M9-minimal medium containing 5 g/L D-glucose and supplemented with 1 mM thiamine (Maniatis, et al., Molecular cloning: a laboratory manual, Cold Spring Harbor Laboratory Press, Cold Spring Harbor, N.Y., 1982). Media was supplemented with 34 µg/ml of chloramphenicol for low copy plasmid propagation and 68 µg/ml of chloramphenicol, 20 µg/ml kanamycin, and 100 µg/ml ampicillin for higher copy plasmid maintenance as necessary. Cell density was monitored spectrophotometrically at 600 nm M9 Minimal salts were purchased from US Biological (Swampscott, Mass.), X-gal was purchased from American Bioanalytical (Natick, Mass.) and all remaining chemicals were from Sigma-Aldrich (St. Louis, Mo.). Primers were purchased from Invitrogen.

Library Construction

A low copy host plasmid (pHACM) was constructed using pUC19 (Yanisch-Perron, et al., *Gene* 33: 103-119, 1985) as a host background strain and replacing ampicillin resistance with chloramphenicol using the CAT gene in pACYC184 (Chang, et al., *J Bacteriol* 134: 1141-1156, 1978) and the pSC101 origin of replication from pSC101 (Bernardi, et al., *Nucleic Acids Res* 12: 9415-9426, 1984). The chloramphenicol gene from pACYC184 was amplified with AatII and AhdI restriction site overhangs using primers CM_sense_AhdI: GTTGCCTGACTCCCCGTCGCCAGGCGTT-TAAGGGCACCAATAAC (SEQ ID NO:1) and CM_anti_AatII: CAGAAGCCACTGGAGCACCTCAAAACTG-CAGT (SEQ ID NO:2). This fragment was digested along with the pUC19 backbone and ligated together to form pUC19-Cm. The pSC101 fragment from pSC101 was amplified with AflIII and NotI restriction site overhangs using primers pSC_sense_AflIII: CCCACATGTCCTAGAC-CTAGCTGCAGGTCGAGGA (SEQ ID NO:3) and pSC_anti_NotI: AAGGAAAAAAGCGGCCGCACGGG-TAAGCCTGTTGATGA TACCGCTGCCTTACT (SEQ ID NO:4). This fragment was digested along with the pUC19-Cm construct and ligated together to form pHACM.

The rpoD gene (EcoGene Accession Number: EG10896; B-number: b3067; SEQ ID NO:27) was amplified from *E. coli* genomic DNA using HindIII and SacI restriction overhangs to target the lacZ gene in pHACM to allow for blue/white screening using primers rpoD_sense_SacI: AAC-CTAGGGAGCTCTGATTTAACGGCTTAAGTGCCGAAG AGC (SEQ ID NO:5) and rpoD_anti_HindIII: TGGAAGCTTTAACGCCTGATCCGGC-CTACCGATTAAT (SEQ ID NO:6). Fragment mutagenesis was performed using the GenemorphII Random Mutagenesis kit (Stratagene, La Jolla, Calif.) using various concentrations of initial template to obtain low, medium, and high mutation rates as described in the product protocol. Following PCR, these fragments were purified using a Qiagen PCR cleanup kit (Qiagen, Valencia, Calif.), digested by HindIII and SacI overnight, ligated overnight into a digested pHACM backbone, and transformed into *E. coli* DH5α competent cells. Cells were plated on LB-agar plates and scraped off to create a liquid library. The total library size of white colonies was approximately $10^5$ to $10^6$.

Phenotype Selection

Samples from the liquid library were placed into challenging environments to select for surviving mutants. For ethanol tolerance, strains were placed in filtered-LB containing 50 g/L of ethanol. These cultures were performed in 30×115 mm closed top centrifuge tubes shaking at 37° C. Strains were plated after 20 hours and selected for individual colony testing. For acetate tolerance, strains were serial subcultured twice in increasing concentrations of acetate starting at 20 g/L and increasing to 30 g/L in M9 minimal media. Cells were then plated onto LB plates and several colonies were selected for single-colony assays. For para-hydroxybenzoic acid (pHBA) tolerance, strains were cultured in 20 g/L of pHBA in M9 minimal media and plated after 20 hours to select for surviving cells. The plasmids from all strains identified with improved phenotypes were recovered and retransformed into a fresh batch of competent cells. Several colonies were selected from each plate to perform biological replicates to verify phenotypes.

Sequence Analysis

Sequences of mutant sigma factors were sequenced using the following set of primers:

```
                                          (SEQ ID NO: 7)
    S1: CCATATGCGGTGTGAAATACCGC, (SEQ ID NO: 8)
    S2: CACAGCTGAAACTTCTTGTCACCC,
```

```
                                          (SEQ ID NO: 9)
    S3: TTGTTGACCCGAACGCAGAAGA, (SEQ ID NO: 10)
    S4: AGAAACCGGCCTGACCATCG, (SEQ ID NO: 11)
    A1: GCTTCGATCTGACGGATACGTTCG, (SEQ ID NO: 12)
    A2: CAGGTTGCGTAGGTGGAGAACTTG, (SEQ ID NO: 13)
    A3: GTGACTGCGACCTTTCGCTTTG, (SEQ ID NO: 14)
    A4: CATCAGATCATCGGCATCCG, (SEQ ID NO: 15)
    A5: GCTTCGGCAGCATCTTCGT,
    and
                                          (SEQ ID NO: 16)
    A6: CGGAAGCGATCACCTATCTGC.
```

Sequences were aligned and compared using Clustal W version 1.82.

Example 1

The main sigma factor, $\sigma^{70}$, was subjected to directed evolution in *E. coli* in search for increased tolerance phenotypes. This main sigma factor was chosen on the premise that mutations will alter promoter preferences and transcription rates and thus modulate the transcriptome at a global level. The rpoD gene and native promoter region were subjected to error-prone PCR and cloned into a low-copy expression vector (FIG. 1). A nearly $10^5$ to $10^6$ viable-mutant library was initially constructed and transformed into strains.

This library was subjected to selection by culturing in the extreme conditions of high ethanol, high acetate and high para-hydroxybenzoic acid (pHBA) concentrations. These conditions were selected because of their industrial relevance: Acetate is an *E. coli* byproduct that is inhibitory to cell growth while prospects for bioethanol production can be enhanced by engineering a strain with increased tolerance to ethanol, thus increasing possible yields (L. O. Ingram et al., *Biotechnol Bioeng* 58, 204-14 (Apr. 5, 1998)). Furthermore, there is considerable industrial interest in the production of pHBA as a precursor for electronic coatings, which is, however, extremely toxic to cells (T. K. Van Dyk, L. J. Templeton, K. A. Cantera, P. L. Sharpe, F. S. Sariaslani, *J Bacteriol* 186, 7196-204 (November, 2004); J. L. Barker, J. W. Frost, *Biotechnol Bioeng* 76, 376-90 (December, 2001)). Each of these tolerance phenotypes has been investigated by traditional methods of randomized cellular mutagenesis, gene complementation and knockout searches, and microarray analysis (R. T. Gill, S. Wildt, Y. T. Yang, S. Ziesman, G. Stephanopoulos, *Proc Natl Acad Sci USA* 99, 7033-8 (May 14, 2002)), with limited success to-date.

Ethanol Tolerance

Figure 2A:
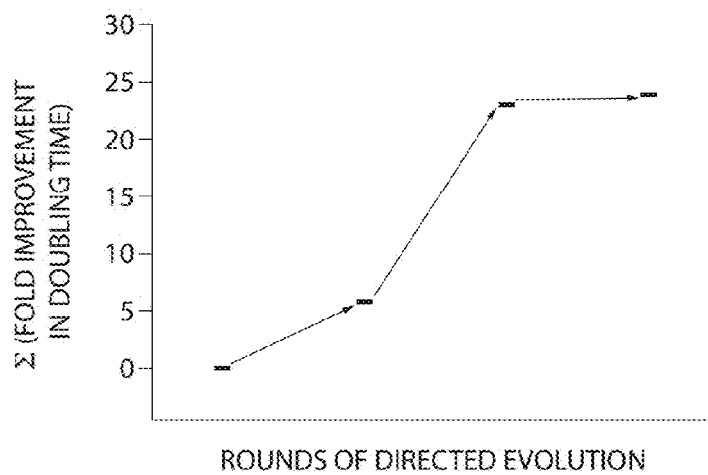

Mutants of the sigma factor library were first selected on the basis of ability to grow in the presence of high concentrations of ethanol in LB complex medium (L. P. Yomano, S. W. York, L. O. Ingram, *J Ind Microbiol Biotechnol* 20, 132-8 (February, 1998)). For this selection, strains were serially subcultured twice at 50 g/L of ethanol overnight, then plated to select for tolerant mutants. A total of 20 colonies were selected and assayed for growth in varying ethanol concentrations. After isolation and validation of improved strains, the best mutant sigma factor was subjected to sequential rounds of evolution. With both subsequent iterations, the selection concentration was increased to 70 and 80 g/L of ethanol. In these enrichment experiments, cells were plated after 4 and 8 hours of incubation due to the strong selection pressure used. Isolated mutants from each round show improved overall growth in various ethanol concentrations (FIG. 2A).

Figure 2B:
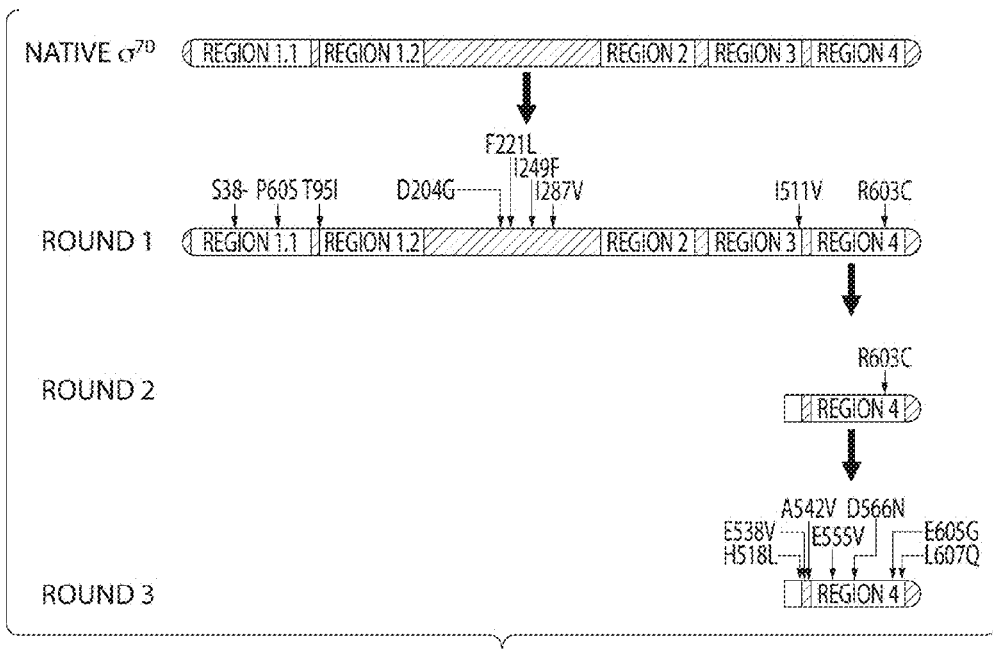

FIG. 2B identifies the sequences of the best mutants isolated from each round of mutagenesis. Sequence alignments of ethanol tolerant sigma factors are provided in FIG. 2D. Interestingly, the second round mutation led to the formation of a truncated factor which is apparently instrumental in increasing overall ethanol fitness. This truncation arose from an artifact in the restriction enzyme digestion and includes part of region 3 and the complete region 4 of the protein. Region 4 is responsible for binding to the promoter region and a truncated form has been previously shown to increase binding affinity relatively to that of the full protein (U. K. Sharma, S. Ravishankar, R. K. Shandil, P. V. K. Praveen, T. S. Balganesh, *J. Bacteriol.* 181, 5855-5859 (1999)). It is therefore possible that this truncated mutant serves to act as a potent and specific inhibitor of transcription by binding to preferred promoter regions and preventing transcription since the remainder of the sigma factor machinery is removed. In the truncated form of the round 2 mutant, the I511V mutation of the first round was reverted back to an isoleucine, leaving only one mutation.

This truncated form was subjected to a third round of mutagenesis and selection to yield a factor with 8 additional mutations. In this final round, the R603c mutation found in the prior two rounds was reverted back to the original residue and many new mutations appeared, leaving only the truncation as the only visible similarity between round 2 and round 3. These rounds of mutagenesis and resulting sequences suggest a difference compared with protein directed evolution. In the latter case, mutations which increase protein function are typically additive in nature. On the other hand, the mutations incurred in altering transcription machinery are not necessarily additive as these factors act as conduits to the transcriptome. In this regard, many local maxima may occur in the sequence space due to the various subsets of gene alterations which may lead to an improved phenotype.

All isolated strains harboring the mutant sigma factors exhibited increased growth rates relative to the control at elevated ethanol concentrations. Furthermore, the growth phenotype of the mutant strains in the absence of ethanol was not impacted (Table 1).

TABLE 1

Directed evolution of ethanol tolerant sigma factors. Improvements in the fold reduction of doubling time are presented for increasing concentrations of ethanol for the three rounds of directed evolution. The mutants in Rounds 2 and 3 show significant increases in the growth rate at higher concentrations of ethanol. A continual increase in the highest concentrations of sustainable cellular growth is seen throughout the rounds of directed evolution.

| Ethanol Concentration (g/L) | Doubling Time (h) Control | Ratio of doubling times ($t_{d,control}/t_{d,engineered\ mutant}$) | | |
|---|---|---|---|---|
| | | Round 1 | Round 2 | Round 3 |
| 0 | 0.76 | 1.01 | 0.98 | 0.98 |
| 20 | 1.31 | 1.68 | 1.63 | 1.63 |
| 40 | 2.41 | 1.64 | 1.30 | 1.54 |
| 50 | 7.24 | 1.92 | 1.82 | 2.06 |
| 60 | 69.3 | 4.53 | 11.70 | 11.18 |
| 70 | 192.3 | 1.40 | 11.56 | 12.43 |
| 80 | ND | ND | 28.64 hours | 29.80 hours |
| Maximum sustainable concentration (g/L) | 40 | 50 | 60 | 70 |

Figure 2C:
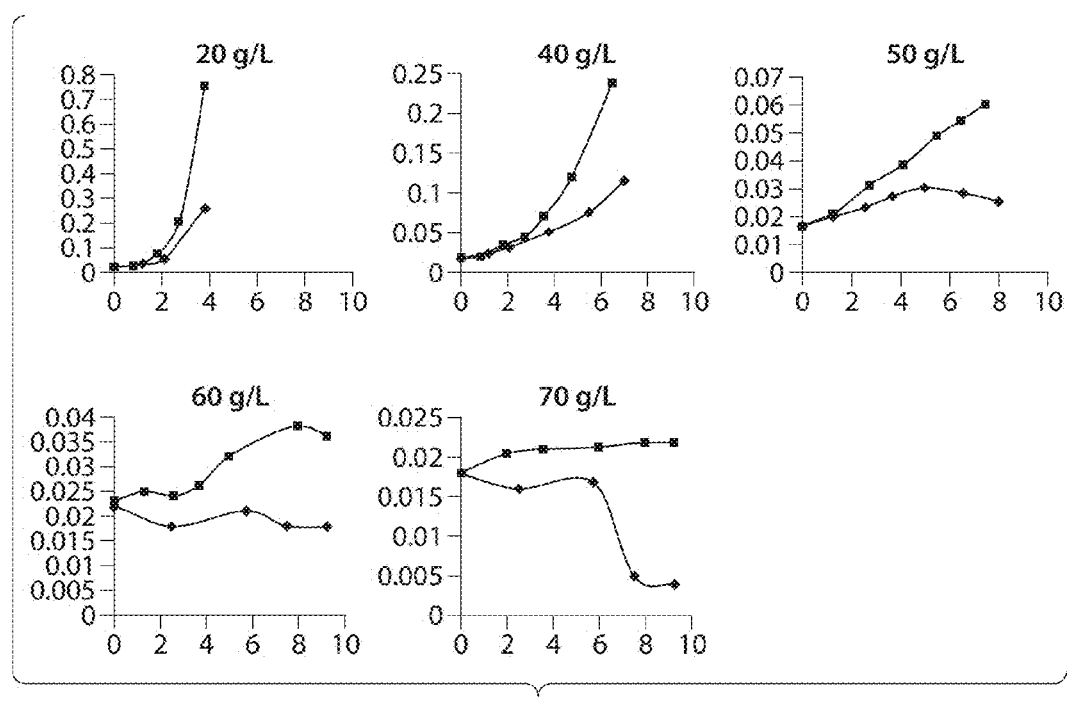

The truncated mutant isolated in the second round showed increased growth rates at higher ethanol concentrations; however, its growth rate was reduced at lower ethanol concentrations compared with the first round mutant. The mutant isolated from the third round showed recovered growth rates, similar to that of the first round, between 20 and 50 g/L of ethanol. Most importantly, each subsequent round increased the highest ethanol concentration at which cells were able to sustain growth for longer than 8 hours, without succumbing to the ethanol toxicity with an accompanying decrease in cell density. The drastic increase in ethanol tolerance obtained through this method is illustrated by the growth curves of the round 3 strain shown in (FIG. 2C) along with those of the wild type control. Sigma factor engineering (SFE) was able to increase the ethanol tolerance beyond the levels previously reported in the literature using more traditional methods. Furthermore, the application of iterative rounds of SFE was illustrated to be capable of further improving the cellular phenotype.

Acetate and pHBA Tolerance

As a second example, the original sigma factor mutant library was serial subcultured twice on 20 g/L followed by 30 g/L of acetate in M9-minimal medium. Single colonies were isolated from this mixture, retransformed to preclude any chromosome-based growth adaptation, and assayed for growth in varying acetate concentrations. Isolated strains showed a drastic increase in tolerance in the presence of high levels of acetate. Additionally, the growth rate was, once again, not substantially affected in the absence of acetate (Table 2). At 30 g/L of acetate, isolated strains had doubling times of 10.5-12.5 hours, approximately ⅕ of the doubling time of the severely inhibited control (56 hours doubling time).

TABLE 2

Application of transcription machinery engineering for additional phenotypes. Mutants were isolated which showed an increased tolerance in either elevated acetate levels or in the presence of high levels of pHBA. Increases in the tolerance are seen at elevated levels of the chemicals, however, no adverse effects are seen in the growth rates or yields in the absence of these chemicals.

| g Acetate concentration (g/L) | Control doubling time (h) | Ratio of doubling times ($t_{d,control}/t_{d,engineered\ mutant}$) | | | | |
|---|---|---|---|---|---|---|
| | | Mutant Ac1 | Mutant Ac2 | Mutant Ac3 | Mutant Ac4 | Mutant Ac5 |
| 0 | 2.11 | 1.00 | 0.98 | 1.10 | 1.03 | 0.97 |
| 10 | 4.99 | 0.88 | 1.02 | 1.05 | 0.99 | 1.08 |
| 20 | 7.23 | 1.32 | 1.16 | 1.17 | 1.17 | 1.28 |

TABLE 2-continued

Application of transcription machinery engineering for additional phenotypes. Mutants were isolated which showed an increased tolerance in either elevated acetate levels or in the presence of high levels of pHBA. Increases in the tolerance are seen at elevated levels of the chemicals, however, no adverse effects are seen in the growth rates or yields in the absence of these chemicals.

| 30 | 56.35 | 4.67 | 4.98 | 4.45 | 4.99 | 5.32 |

| pHBA Concentration (g/L) | Control (OD at 13 h) | Mutant HBA1 (Ratio) |
|---|---|---|
| 0 | 1.14 | 0.97 |
| 5 | 0.56 | 1.17 |
| 10 | 0.35 | 1.21 |
| 15 | 0.097 | 1.55 |
| 20 | ND | ND |

Figure 3A:
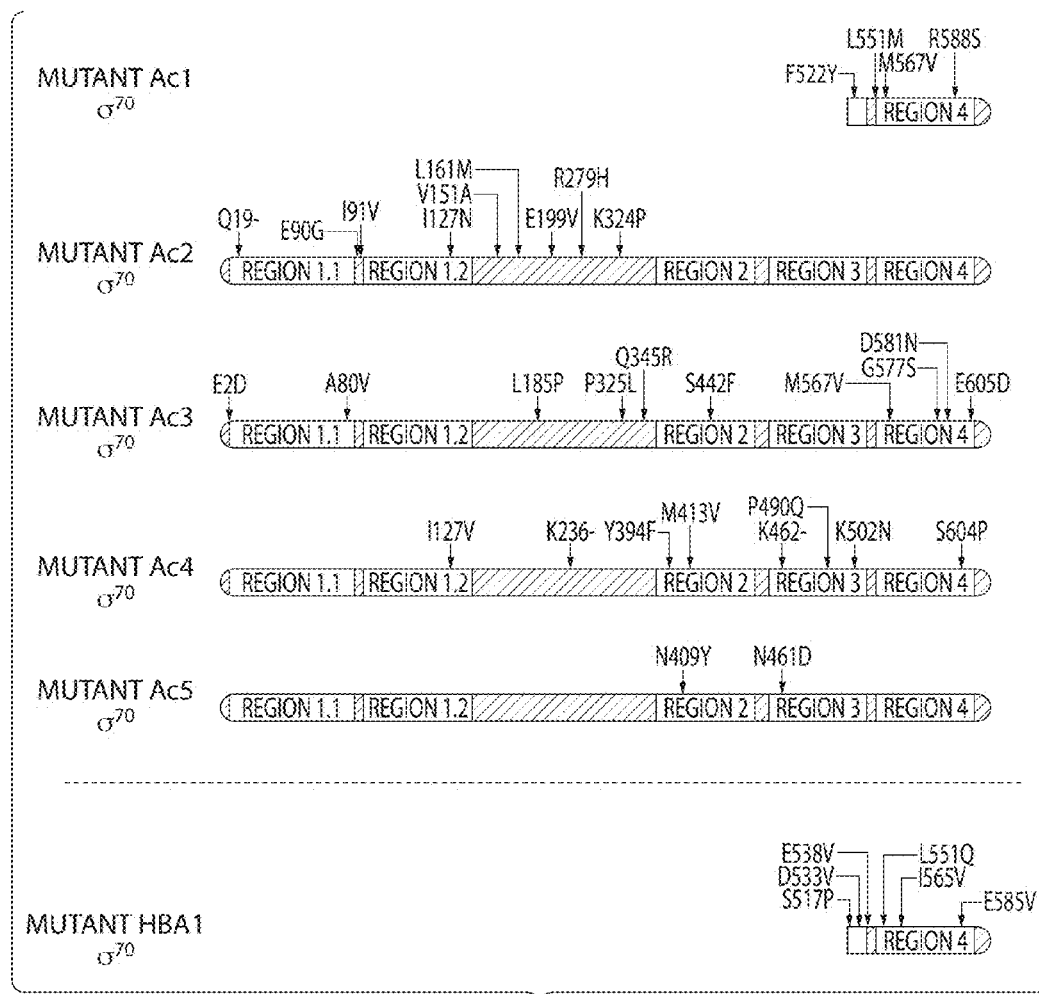

FIG. 3A summarizes the various mutations classified by region in the isolated sigma factors eliciting an increased cellular tolerance for acetate. Sequence alignments of acetate tolerant sigma factors are provided in FIG. 3B. Only one of the five isolated mutants was truncated. The M567V mutation appeared in two of the acetate mutants and most of the mutations appear to be distributed among the functional domains of the sigma factor. It is interesting to note that even though strains have similar tolerance profiles, the underlying mutations are different suggesting different molecular mechanisms influencing the transcription profiles.

As a another example, the mutant library was cultured in the presence of 20 g/L of pHBA to select for strains with increased tolerance to this compound in terms of growth and viability at high pHBA concentrations. One strain was isolated with marked improvement in the growth yield at 13 hours compared with the control and essentially unchanged growth phenotype in the absence of pHBA (Table 2). Mutant HBA1 showed a truncated form of the sigma factor with a total of six mutations (FIG. 3A), with 4 of 6 residues being changed to a valine. Sequence alignments of pHBA tolerant sigma factors are provided in FIG. 3C.

These examples illustrate the potential of sigma factor engineering to introduce global transcriptome changes that allow the organism to access novel cellular phenotypes. Recently, we have successfully extended the concept of global transcription machinery engineering beyond tolerance phenotypes to select for mutants which increase metabolite overproduction rates (see below). Furthermore, this concept has been explored with other host systems including eukaryotic transcription machinery components. In each of these examples, the global changes brought about by random mutations in the components of transcriptional regulatory machinery is shown to improve to cellular phenotypes beyond levels attainable through rational engineering or traditional strain improvement by random mutagenesis.

For the first time, we demonstrated the application of directed evolution to alter the global transcription machinery. This strategy allowed for the directed modification of the genetic control of multiple genes simultaneously, as opposed to typical consecutive, gene-by-gene strategies. Furthermore, we found the paradigm of directed evolution to be applicable as it allowed sequential phenotypic improvements by probing deeper into the vast sequence space of transcription factor engineering. As a result, it is now possible to unlock complex phenotypes regulated by multiple genes which would be very unlikely to reach by the relatively inefficient iterative search strategies.

It is worth noting that the described method can also be applied in reverse to uncover the complicated interactions of the genotype-phenotype landscape. In such applications, one would employ a number of high-throughput cellular and molecular assays to assess the altered cellular state and ultimately deduce systematic mechanisms of action underlying the observed phenotype in these mutants. The application of directed evolution to global transcription machinery as described here is a paradigm shifting method for identifying genetic targets, eliciting desired phenotypes and realizing the goal of whole cell engineering.

Example 2

Organic Solvent Tolerance

Figure 4:
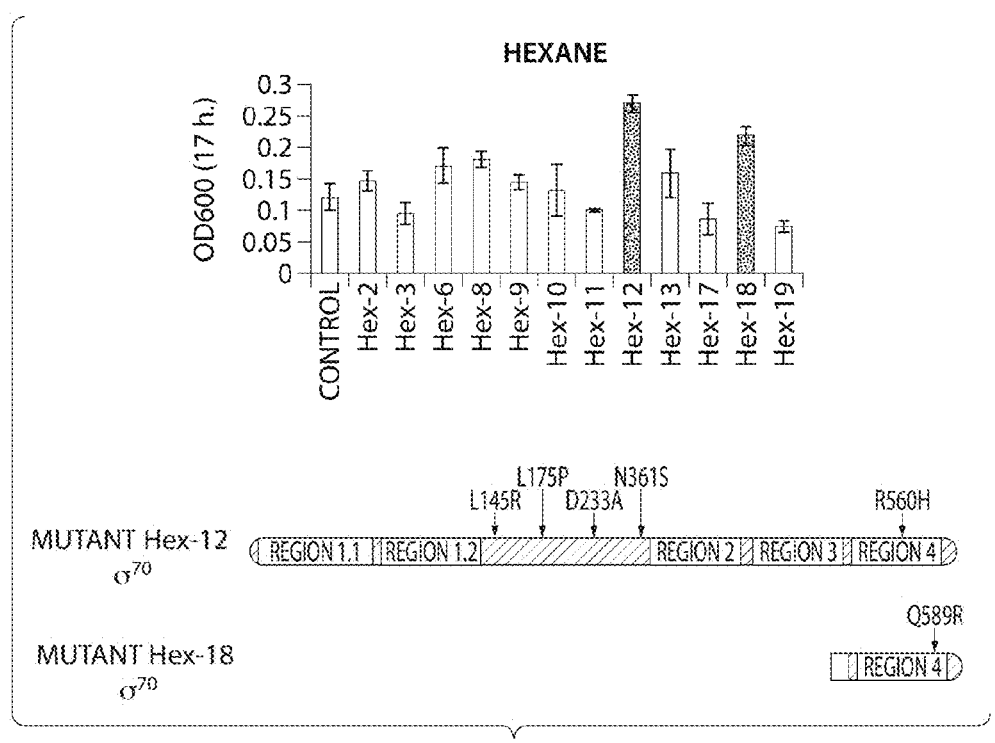
FIG. 4 depicts cell densities of cultures of isolated strains with hexane tolerant sigma factor mutants.

The application of global transcription machinery engineering has been extended to include additional tolerance phenotypes. Bacterial strain tolerance to organic solvents is useful in several situations: (1) bioremediation of hazardous waste, (2) bioproduction of organic solvents from bacteria, and (3) bioprocessing applications requiring a two-phase reactor (i.e. extractive fermentations to continuously remove hydrophobic products operation). To investigate the potential to increase solvent tolerance in E. coli, the original rpoD ($\sigma^{70}$) mutant library was cultured and harvested in exponential phase and transferred to a two-phase system containing LB medium and hexanes (10% v/v). Strains were isolated after 18 hours of growth in the presence of hexane. These individual colonies were again cultured to exponential phase and then cultured in the presence of hexane. Cell densities are measured after 17 hours. Cell densities from culture with hexane are shown in FIG. 4. The strains shown in FIG. 4 are re-transformed strains performed in biological replicates. All selected strains had an increase in cell density over the control strain containing an unmutated version of the rpoD gene. Furthermore, PCR analysis indicated that mutant strains Hex-3, Hex-8, Hex-11, Hex-12, Hex-13, Hex-17 and Hex-19 have a whole version of the sigma factor while strains Hex-2, Hex-6, Hex-9, Hex-10, and Hex-18 have a truncated version. FIG. 4 also shows the sequence (location of mutations) for the two best-performing mutants, Hex-12 and Hex-18.

Figure 5:
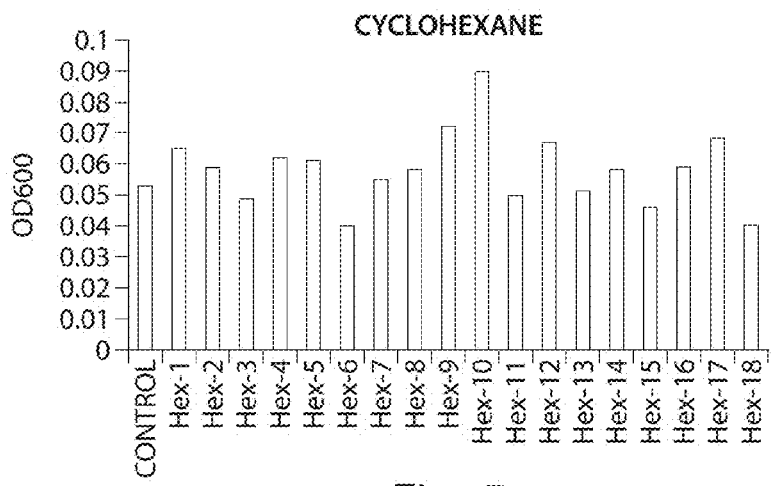
FIG. 5 shows cell densities of cultures of isolated strains with cyclohexane tolerant sigma factor mutants.

Additionally, these strains were tested for growth in the presence of cyclohexane, which is known to be a more toxic organic solvent to microorganisms than hexane. FIG. 5 shows the cell densities from cultures with cyclohexane. Several of the strains isolated from the hexane selection also showed and increase in cell density over the control.

Example 3

Antibiotic Resistance

Figure 6:
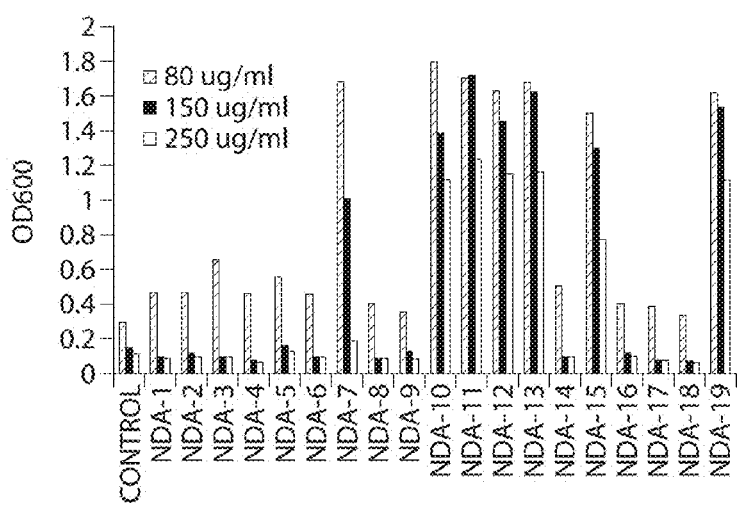
FIG. 6 depicts cell densities of cultures of isolated strains of antibiotic resistant sigma factor mutants at increasing concentrations of nalidixic acid.
Figure 7A:
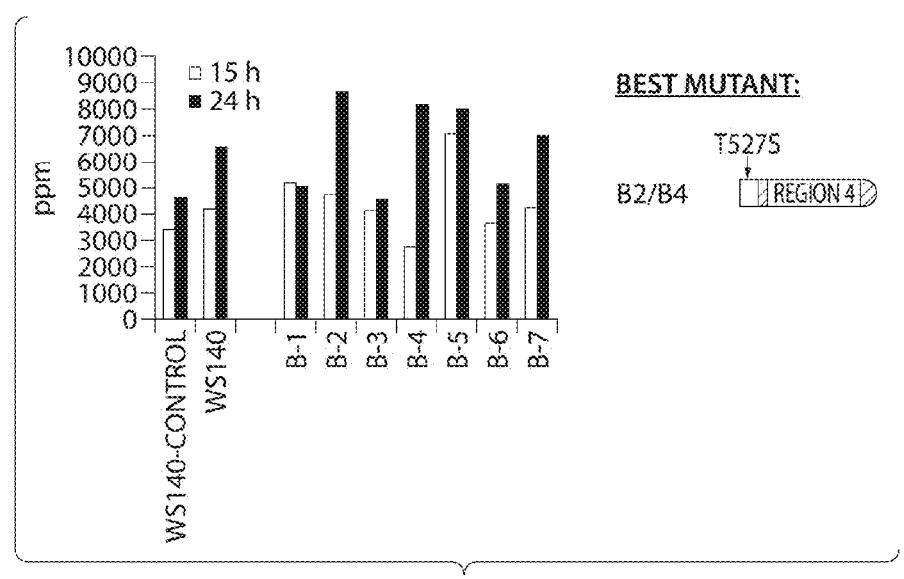
FIGS. 7A-7D show the results of culturing and assaying selected strains for lycopene production at 15 and 24 hours, along with the sequence of the sigma factor mutant from the best strain.
Figure 7B:
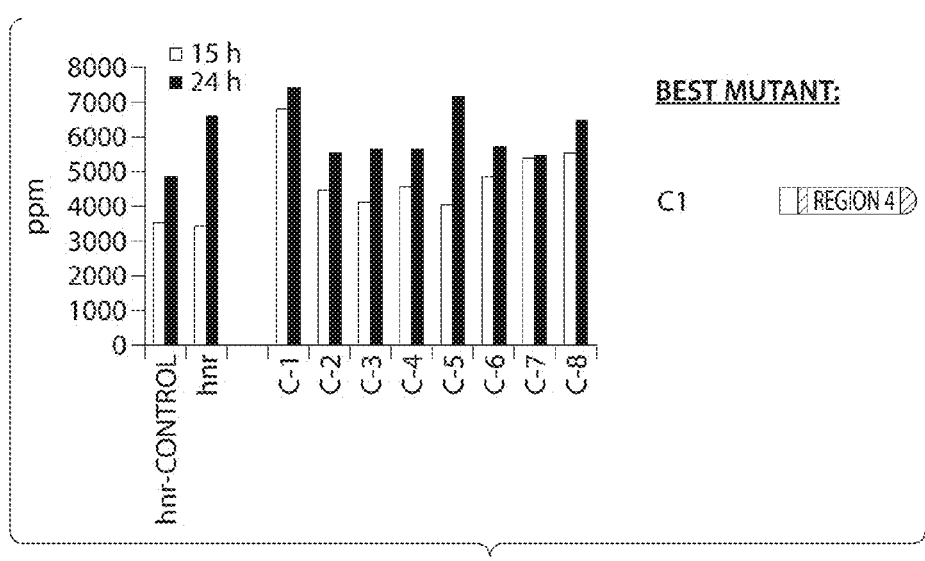
Figure 7C:
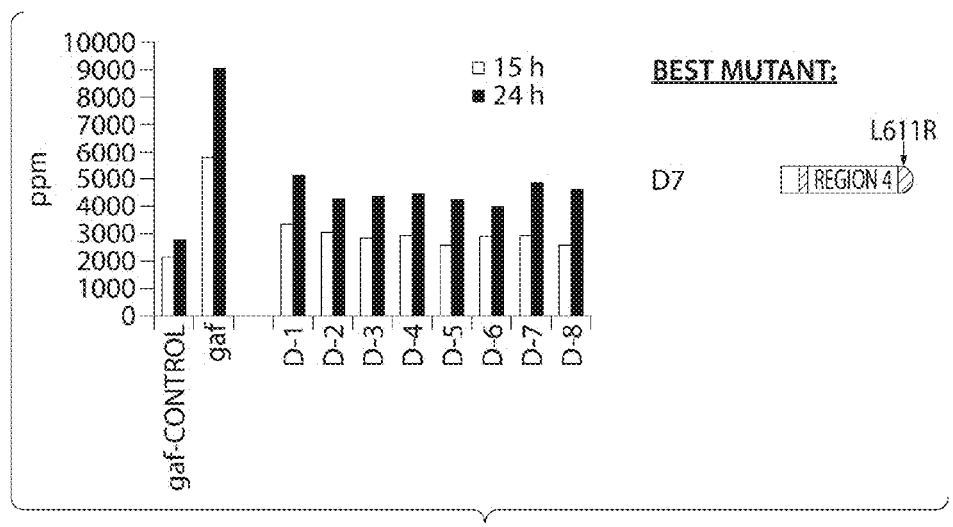
Figure 7D:
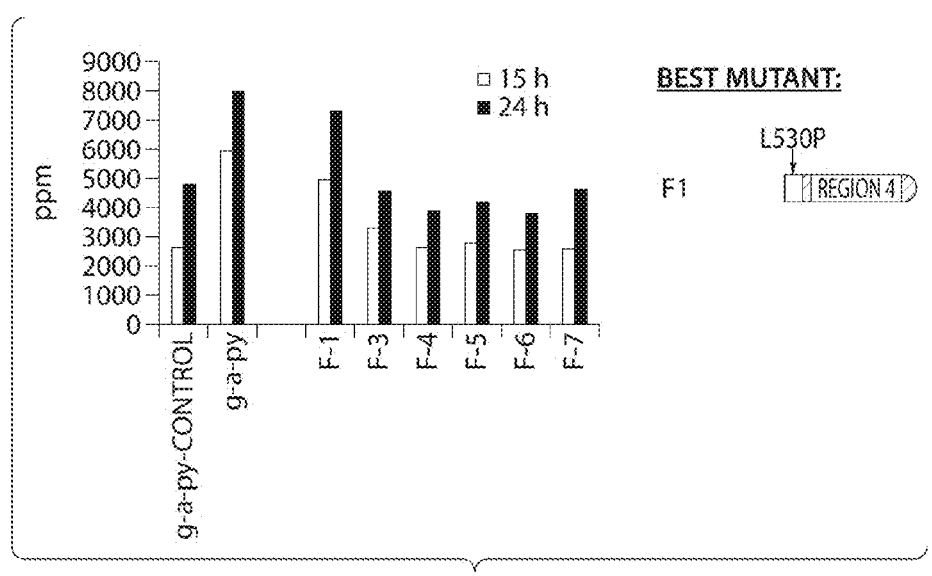

The application of global transcription machinery engineering has been extended to include antibiotic resistance. Antibiotic resistance among microorganisms is becoming a significant problem placing a stress on health care and pharmaceutical companies to find alternatives ways to fight infections. Many resistant strains are known to contain specific genes encoding for a resistance. However, before microorganisms are able to evolve such a gene, they must first gain an initial resistance in an effort to persist in the presence of antibiotics. While incurring random mutations in the genome is one alternative, cells can also change their gene expression in response to these antibiotics. The use of global transcription machinery engineering was tested to identify the possibility of creating antibiotic resistant strains. This phenotype would ultimately be controlled by the altered expression of the transcriptome, mediated through the mutant transcription machinery. An analysis of the gene expression of these strains could lead to the identification of novel gene targets and enzymes which control the resistance of the strain. These targets could then lead to the development of small molecule drugs which inhibit or enhance the activity of the identified enzymes. The topic of antibiotic resistance was tested by culturing the mutant sigma factor library in the presence of 250 µg/ml of nalidixic acid, a quinolone (the same family of drugs as Ciprofloxacin), which is in excess of the minimum inhibitory concentration of the control of around 80 µg/ml. FIG. 6 presents the cell density (OD600) for various isolated strains at increasing concentrations of nalidixic acid. Several isolated strains showed significant growth in the presence of high concentrations of nalidixic acid. These strains are tested for verification after transformation of the plasmids into fresh host strains. Furthermore, these mutants are sequenced; PCR analysis indicated that mutant strains NdA-7 and NdA-15 are whole length sigma factors while NdA-10, NdA-11, NdA-12 and NdA-13 are truncated versions.

Example 4

Metabolite Overproduction Phenotypes

The basic tenet of global transcription machinery engineering is the ability to create multiple and simultaneous gene expression modifications. Previously, this method was successfully employed for the identification of mutants with increased tolerance phenotypes. In these subsequent examples, a mutant library of the principal sigma factor, encoded by rpoD, was examined for its capacity to enhance metabolite overproduction phenotypes beyond those levels achievable by single genetic modifications.

Lycopene Production

Previously, we have identified a number of single and multiple gene knockout targets which showed an increase of lycopene production in the background of a pre-engineereed strain (Alper et al., *Nat Biotechnol* 2005 and Alper et al., *Metab Eng* 2005). In this study, we sought to utilize the technique of global transcription machinery engineering to enhance lycopene production. Utilizing several available strain backgrounds which were previously engineered along with the parental strain, it was possible search for mutant factors, independently in each background, which resulted in an increased lycopene production. For this study, the parental strain, Δhnr, and the two identified global maximum strains, ΔgdhAΔaceEΔfdhF, and ΔgdhAΔaceEΔ$_P$yjiD, were selected. The best mutant from each of the four tested genetic backgrounds was then swapped to investigate the landscape created by mixing 4 strains with the 4 identified mutant sigma factors.

Identification of Mutant Sigma Factors

The mutant sigma factor library was transformed into each of the four strains and selected based on lycopene production on minimal medium plates supplemented with 5 g/L of glucose. Selected strains were then cultured and assayed for lycopene production at 15 and 24 hours using M9 medium. FIGS. 7A-7D illustrate the results of these searches along with the sequence of sigma factor mutant from the best strain. Lycopene production is indicated for the strain with and without the control plasmid. For some backgrounds, this control plasmid resulted in a large decrease in lycopene production over the strain absent of this plasmid. It is interesting to note that all of these identified factors have been truncated. Furthermore, the mutant identified from the hnr knockout background was simply truncated and contained no mutations. Given the suspected mode of action for this truncation, it is possible that this mutant factor essentially suppresses all of the normal genes expressed under the control of rpoD. In an hnr mutant, a higher steady state level of the stationary phase sigma factor, $\sigma^s$, is available to take over the remainder of transcription. Furthermore, the second highest mutant in this background resulted in a full length sigma factor containing several mutations.

Combinations of Strains and Identified Mutant Factors

Figure 8:
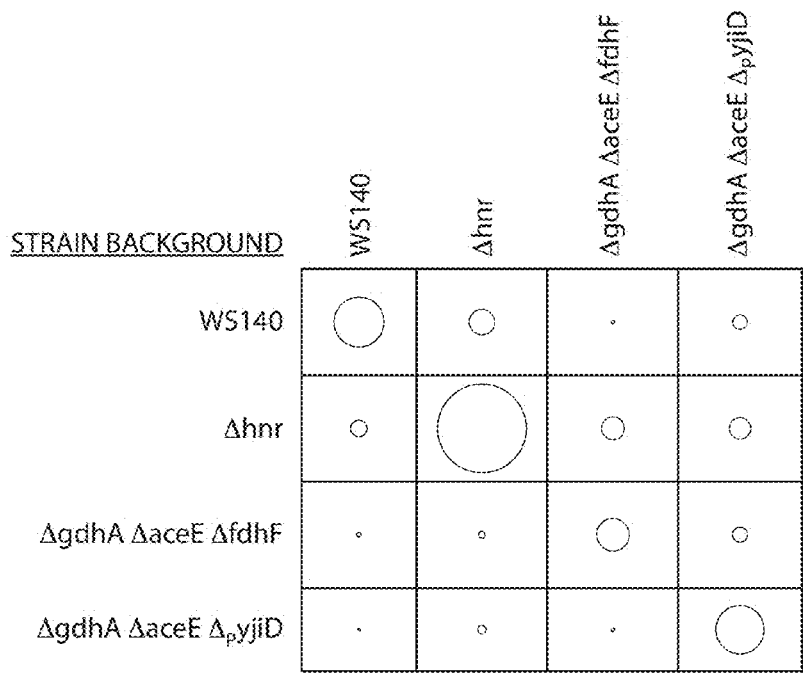
FIG. 8 is a dot plot that depicts the maximum fold increase in lycopene production achieved over the control during the fermentation. The size of the circle is proportional to the fold increase.

The four strains with varying genetic backgrounds were then combined with the four independently identified mutant sigma factors to examine the resulting 16 strain landscape. It is interesting to initially note that none of the identified mutants in FIGS. 7A-7D which were sequenced for a given genetic background overlapped with those identified in another genetic background. As a result, it is initially suspected that the landscape would be diagonally dominant, indicating that the effect elicited by the mutant factor is specific to the genetic background. These 16 strains along with the controls were cultured in a 2×M9 medium with staged glucose feed. The lycopene level was assayed at 15, 24, 39, and 48 hour timepoints. FIG. 8 presents a dot plot which depicts the maximum fold increase in lycopene production achieved over the control during the fermentation. The size of the circle is proportional to the fold increase. As suspected, the landscape is clearly diagonally-dominant with mutant factors predominantly working in the strain background in which they were identified.

Figure 9:
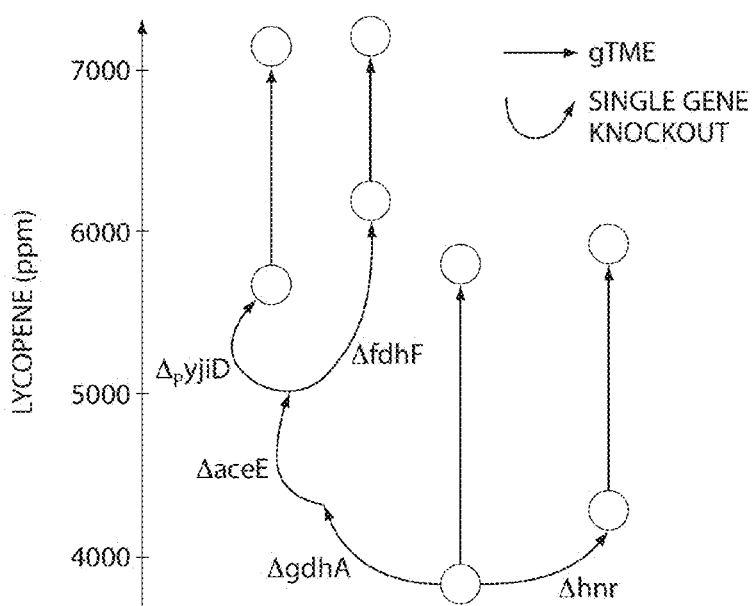
FIG. 9 illustrates the lycopene content after 15 hours for several strains of interest. This figure compares the improvement provided by global transcription machinery engineering to traditional methods of strain improvement by sequential gene knockouts. In this example, the method of global transcription machinery engineering was more potent in increasing the phenotype than a series of multiple gene knockouts. Furthermore, improvements were achieved in pre-engineered strains.

FIG. 9 illustrates the lycopene content after 15 hours for several strains of interest. The single round of mutagenesis in both the parental strain and hnr knockout was able to achieve similar results as strains previously engineered through the introduction of three distinct gene knockouts. However, in these backgrounds, lycopene levels were able to be further increased through the introduction of an additional mutant sigma factor.

These results indicate that (1) global transcription machinery engineering (gTME) is able to elicit metabolic phenotypes and, more importantly, (2) a single round of selection using gTME is more effective than a single knockout or overexpression modification. Furthermore, the identified mutant is not generally transferable across strain backgrounds, which suggests that there may be different modes of lycopene production in each of the strains. As an example of these modes, the maximum fold difference in the wild type strain was realized after only 15 hours and then converged with the control strain by the end of the fermentation. Conversely, the mutant factor in the ΔgdhAΔaceEΔ$_P$yjiD strain progressively increased in lycopene content compared with the control for increasing timepoints. Nevertheless, the highest lycopene production resulted in using gTME in the background of a previously engineered strain indicating that, given only one round of selection, it is better to start in an optimized strain. However, the results of ethanol tolerance suggest that it is possible to achieve continual improvements in fitness through the application of directed evolution, indicating that it may be possible to increase lycopene production further.

Bioproduction of Polyhydroxybutyrate (PHB)

The application of global transcription machinery engineering has been extended to include a further example of metabolite overproduction. An additional metabolic phenotype (in addition to production of lycopene), bioproduction of polyhydroxybutyrate (PHB), was investigated using transcription machinery engineering. PHB is produced from the precursor molecule of acetyl-coA.

Materials/Methods

*Escherichia coli* (XL-1 Blue, Stratagene, La Jolla, Calif.) transformed with a modified pJOE7 (Lawrence, A. G., J.

Choi, C. Rha, J. Stubbe, and A. J. Sinskey. 2005. *Biomacromolecules* 6:2113-2119) plasmid was cultured at 37° C. in Luria-Bertani (LB) medium containing 20 g/L glucose and 25 is μg/mL kanamycin. The modified pJOE7 was graciously given to us by Dr. Anthony Sinskey (MIT, Cambridge, Mass.) and contains phaAB from *C. necator* and the phEC from *Allochromatium vinosum* and encodes kanamycin resistance. As a no PHB control, the same plasmid without the pha genes was also cultured. Optical density was used to track cell growth using an Ultraspec 2100 pro (Amersham Biosciences, Uppsala, Sweden).

Staining and Flow Cytometry

A nile red (Sigma-Aldrich, St. Louis, Mo.) stock solution was made by dissolving to 1 mg/mL in dimethyl sulfoxide unless otherwise noted. 3 μL of stock solution was added to 1 mL of staining buffer as indicated in the staining optimization. Flow cytometry was carried out on a FACScan (Becton Dickinson, Mountain View, Calif.) using the following settings; *Synechocystis* FSC=E00, SSC=411, FL-1=582, FL-2=551 and *E. coli* FSC=E00, SSC=411, FL-1=582, FL-2=535. Cells were excited with an air-cooled argon ion laser (488 nm), and FL-2 (585 nm) was used to detect nile red fluorescence. Flow cytometry analysis was done on 50,000 cells using WinMDI 2.8.

Staining effectiveness was characterized by resolution, $R_S$ (Eq. 1), where $M_n$ is the geometric mean of the fluorescence distribution of n (n=1 is the PHB producing cell, n=2 is the no PHB control). $\delta_n$ is the standard deviation of the fluorescence distribution. $R_S$ is a quantitative measure of the ability to differentiate two populations.

$$R_S = \frac{2(M_1 - M_2)}{\delta_1 + \delta_2} \quad (1)$$

Cell viability was accessed by ratio of the cfu in the final stained preparation to cells from the media.

Chemical PHB Analysis

PHB was analyzed as shown previously (Taroncher-Oldenburg, G., and G. Stephanopoulos. 2000. *Applied Microbiology and Biotechnology* 54:677-680). >10 mg of cells was collected from culture by centrifugation (10 mM, 3,200×g). The resulting pellet was washed once with cold deionized H$_2$O and dried overnight at 80° C. The dry pellets were boiled in 1 ml of concentrated H$_2$SO$_4$ for 60 min, diluted with 4 ml of 0.014 M H$_2$SO$_4$. Samples were centrifuged (15 mM, 18,000×g) to remove cell debris, and liquid was analyzed by HPLC using an Aminex HPX-87H ion-exclusion column (300×7.8 mm; Bio-Rad, Hercules, Calif.) (Karr, D. B., J. K. Waters, and D. W. Emerich. 1983. *Applied and Environmental Microbiology* 46:1339-1344). Commercially available PHB (Sigma-Aldrich, St. Louis, Mo.), processed in parallel with the samples, was used as standards.

*E. coli* Staining Optimization

*E. coli* XL1-blue harboring the modified pJOE and the no PHB control were cultured as described.

Shock Optimization: Cultures were grown to stationary phase. A variety of different permeabilization methods were tested for resolution and viability after the shock. Sucrose shock was carried out as shown previously (Vazquez-Laslop, N., H. Lee, R. Hu, and A. A. Neyfakh. 2001. *J. Bacteriol.* 183:2399-2404). 1 mL of cells was cooled to 4° C. for 10 min. The cells were then centrifuged (3 mM, 3000×g, 4° C.) and resuspended in 1 mL ice-cold TSE buffer (10 mM Tris-Cl [pH=7.5], 20% sucrose, 2.5 mM Na-EDTA). The cells were incubated on ice for 10 min then resuspended (3 mM, 3000×g, 4° C.) in 1 mL deionized water with 3 μL nile red stock solution. Cells were stained in the dark for 30 min and analyzed on the FACScan. Isopropanol shocked cells were centrifuged (3 min, 3000×g) and resuspended in 70% isopropanol for 15 min. Cells were then centrifuged (3 min, 3000×g) and resuspended in deionized water with 3 μL nile red stock solution. Cells were incubated for 30 min in the dark and analyzed on the FACScan. DMSO shock was performed by centrifuging (3 min, 3000×g) 1 mL of cell culture. 50 μL of nile red stock solution was added directly to the pellet. The pellet was quickly vortexed and diluted to 1 mL in water after incubating for 30 s. Cells were incubated for 30 min in dark and analyzed on the FACScan. Heat shock was performed as in competent cell preparation (Sambrook, J., E. F. Fritsch, and T. Maniatis. 1989. *Molecular Cloning: A Laboratory Manual*, 2nd ed. Cold Spring Harbor Laboratory Press). 1 mL of cells was cooled for 10 min. Cells were then centrifuged (3 mM, 3000×g, 4° C.), and resuspended in 1 mL cold 80 mM MgCl$_2$/20 mM CaCl$_2$. Cells were centrifuged (3 min, 3000×g, 4° C.) and resuspended in 1 mL 0.1 M CaCl$_2$ with 3 μL nile red stock solution. Cells were heat shocked at 42° C. for 90 s. Cells were incubated for 30 min in dark then analyzed on the FACScan.

Concentration Optimization: Cells were prepared by sucrose shock using 3 μL of different nile red solutions to a final concentration between 30-30,000 ng/mL.

Sucrose Concentration Optimization: Cells were prepared by sucrose shock using TSE buffer with varying sucrose concentrations (0, 5, 10, 15, 20%).

Figure 10A:
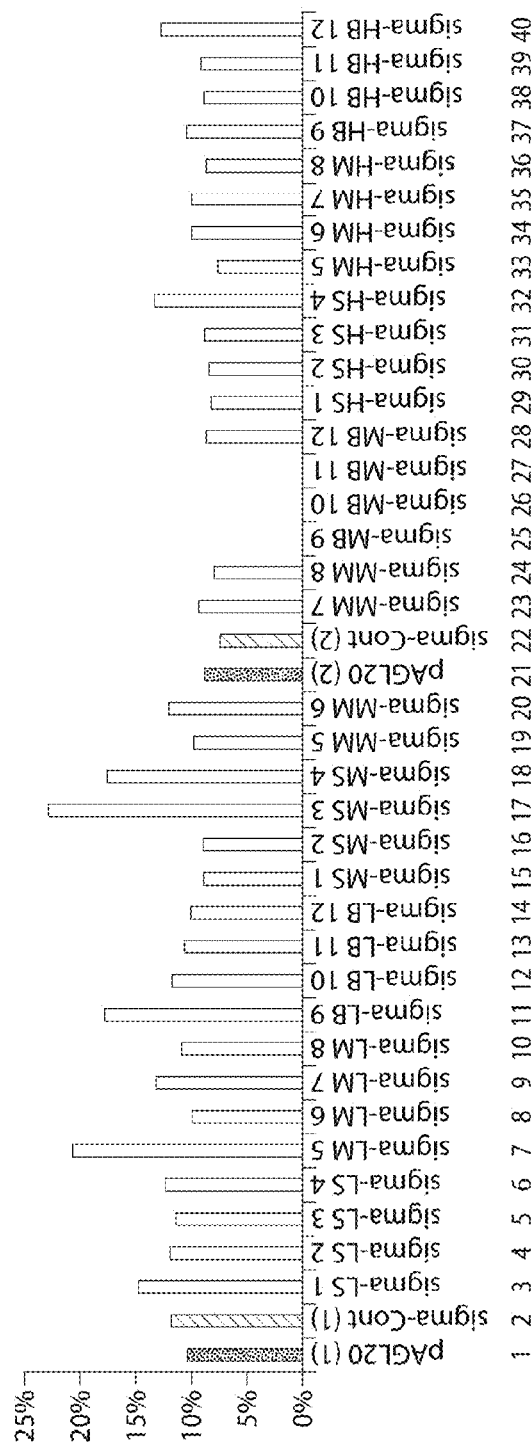
FIGS. 10A-10B show strains selected for increased exponential phase PHB in a glucose-minimal media.
Figure 10B:
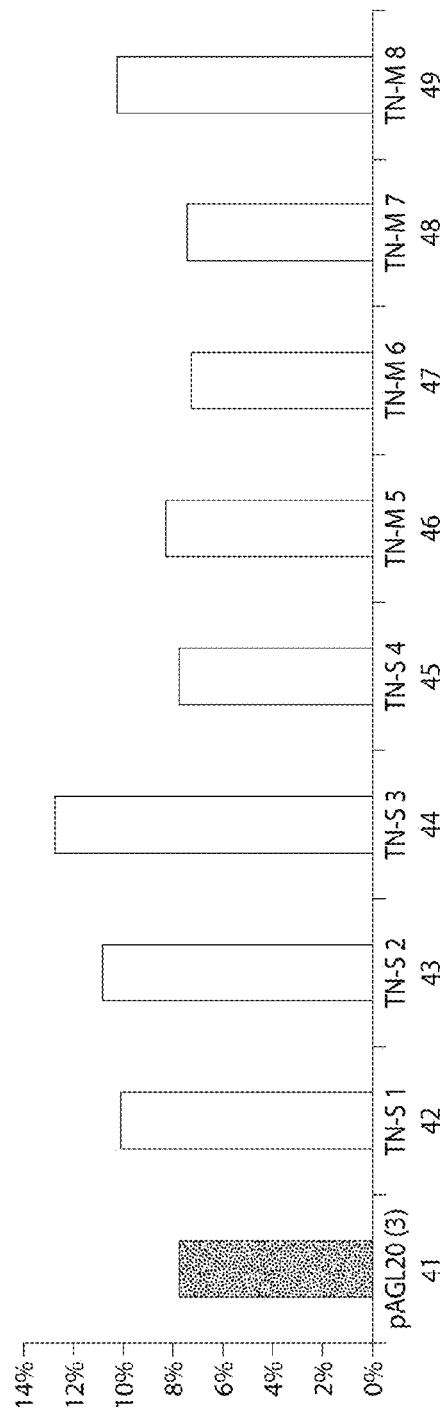

The mutant sigma factor library was introduced into *Escherichia coli* as described above. Strains were selected for increased exponential phase PHB in a glucose-minimal media. Additionally, a random knockout library created using transposon mutagenesis was also tested to compare the efficacy of transcription machinery engineering to that of traditional strain improvement methods. FIG. 10A presents the data for various strains (bars in red and yellow represent controls) obtained using sigma factor engineering. In comparison, FIG. 10B presents the results of selected strains from a random knockout library. Several mutants obtained using sigma factor engineering produced nearly 25% dcw (dry cell weight) of PHB. The best strain obtained in one round of sigma factor engineering was far superior to the best strain obtained using random knockouts. A second round of mutagenesis in the background of the best mutant is carried out as described above for further improvement of the PHB phenotype.

Example 5

Library Diversity and Construction

The size and breadth of the sigma factor library is increased in one or more of the following ways.

(1) The library includes not only the main sigma factor of *E. coli* ($\sigma^{70}$, encoded by rpoD), but also one or more alternative forms, e.g., rpoS, rpoF, rpoH, rpoN, rpoE and/or fecI.

It may be possible to further improve phenotypes and search for optimized strains through the simultaneous introduction of multiple mutant versions of transcription machinery units. The mutated sigma factor genes (or other global transcription machinery) are expressed, for example, using expression cassettes which coexpress two or more of these to genes. The two or more genes may be two or more of the same type of transcription machinery (e.g., two versions of an rpoD) or may be two or more distinct transcription machinery (e.g., rpoD and rpoS).

Likewise, more than one different mutant versions of global transcription machinery may be beneficial to properly optimize for a phenotype. For example, multiple mutated sigma 70 (rpoD) genes can be coexpressed.

(2) In addition to random mutations introduced by error prone PCR as described above, the library includes all possible truncations from both the C terminus and N terminus and combinations thereof.

(3) Furthermore, the library includes alternative chimeras of various regions of the sigma factors by artificially fusing the regions. For example, Region 1 of sigma factor 70 is used to replace Region 1 of sigma factor 38. A similar approach by using DNA shuffling to create diversity is well known in the art (e.g., gene shuffling patents of W. Stemmer et al., assigned to Maxygen; see listing at maxygen.com/science-patents).

(4) Sigma factors from other bacteria are included in the library in the same configurations (e.g., random mutations, truncations, chimeras, shuffling) as described for *E. coli* sigma factor 70 above. These factors may possess unique properties of DNA binding and may help to create a diversity of transcriptome changes.

Example 6

Global Transcription Machinery Engineering in Eukaryotic Cells

The directed evolution of global transcription machinery is applied to yeast and mammalian systems (e.g., CHO, HeLa, Hek cell lines) for enhanced recombinant protein production and resistance to apoptosis in inducing conditions.

A gene encoding global transcription machinery (e.g., TFIID) is subjected to error prone PCR, truncation and/or DNA shuffling in order to create a diverse library of global transcription machinery mutants. The library is introduced into the yeast or mammalian cells and, in a first experiment, the production of recombinant protein by the cells is examined. A readily assayable protein is preferred for these experiments, such as SEAP or a fluorescent protein (e.g., GFP). In the case of fluorescent proteins, cells can be selected using a fluorescence activated cell sorter or if grown in multiwell plates, a fluorescence plate reader can be used to determine the enhancement in protein production.

In a second experiment, anti-apoptosis phenotypes are examined in the yeast or mammalian cells.

Example 7

SDS Tolerance

The directed evolution of global transcription machinery was applied to the problem of cellular tolerance to sodium dodecyl sulfate (SDS).

Figure 11:
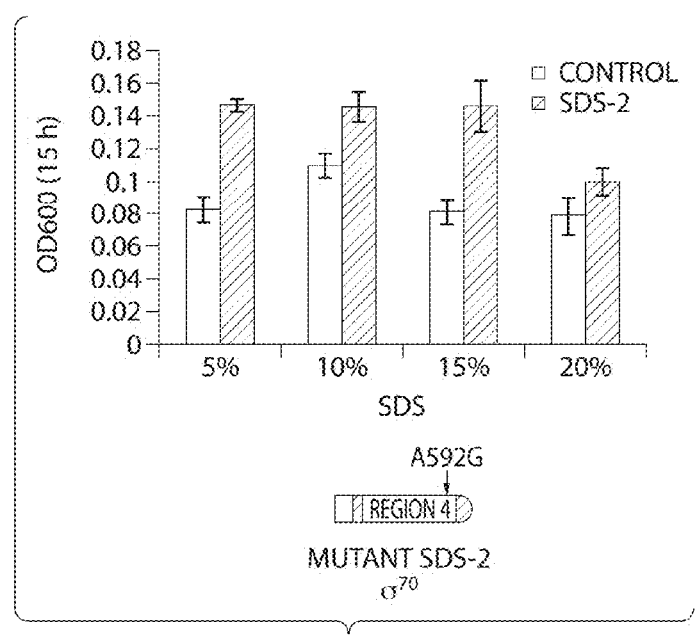
FIG. 11 depicts cell densities of cultures of isolated strains of SDS-tolerant sigma factor mutants at increasing concentrations of SDS, along with the sequence of the sigma factor mutant from the best strain.

The mutant rpoD library was transformed into *Escherichia coli* DH5α, which were then subcultured in LB medium containing increasing amounts of SDS (5%, then 15% SDS, by mass). Strains were selected for increased tolerance in SDS. Strain SDS-2 was selected and retransformed to verify the phenotype. Strain SDS-2 was then tested at 5-20% SDS (by mass). This mutant was found to have increased growth at elevated SDS levels, without any detrimental effects to the growth in the absence of SDS. FIG. 11 shows the cell densities of cultures of isolated strains of SDS-tolerant sigma factor mutants at increasing concentrations of SDS, along with the sequence of the sigma factor mutant from the best strain.

Example 8

Engineering Multiple Phenotypes

Global transcription machinery engineering was applied to the problem of imparting a multiple tolerance phenotype in *E. coli*. In order to obtain the tolerance to both ethanol and SDS, in a first set of experiments, strains were isolated following three alternative strategies: (i) mutants were isolated after treatment/selection in both ethanol and SDS, (ii) mutants were isolated which were tolerant to ethanol first, then subjected to an additional round of mutagenesis and selected using an ethanol/SDS mixture, and (iii) mutants were isolated which were tolerant to SDS first, then subjected to an additional round of mutagenesis and selected using an ethanol/SDS mixture. These strains were tested for growth in the presence of various concentrations of ethanol and SDS to obtain growth curves and to assess the effectiveness of these strategies. The experiments were conducted using the protocols described in other examples above.

In a second set of experiments, a mutant sigma factor is isolated from an ethanol tolerant strain and is co-expressed with a mutant sigma factor that is isolated from an SDS tolerant strain. These experiments are conducted using the protocols described in other examples above.

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

We claim:

1. A method for altering the phenotype of a cell comprising:
    mutating a nucleic acid encoding global transcription machinery and, optionally, its promoter,
    expressing the nucleic acid in a cell to provide an altered cell that includes mutated global transcription machinery,
    culturing the altered cell, and
    selecting the altered cell for a predetermined phenotype, wherein the phenotype is tolerance of high sugar concentration; tolerance of a plurality of deleterious conditions; or tolerance to a toxic substrate, metabolic intermediate or product.

2. The method of claim 1, further comprising determining the phenotype of the altered cell.

3. The method of claim 1, wherein the cell is a prokaryotic cell.

4. The method of claim 3, wherein the global transcription machinery is a sigma factor or an anti-sigma factor.

5. The method of claim 1, wherein the cell is a eukaryotic cell.

6. The method of claim 5, wherein the global transcription machinery binds to an RNA polymerase I, an RNA polymerase II or an RNA polymerase III, or a promoter of an RNA polymerase I, an RNA polymerase II or an RNA polymerase III.

7. The method of claim 1, wherein the nucleic acid is part of an expression vector.

8. The method of claim 1, wherein the nucleic acid is a member of a collection of nucleic acids.

9. The method of claim 1, wherein the step of expressing the nucleic acid comprises integrating the nucleic acid into the genome or replacing a nucleic acid that encodes the endogenous global transcription machinery.

10. The method of claim 1, wherein the mutation of the nucleic acid comprises directed evolution of the nucleic acid.

11. The method of claim 1, wherein the nucleic acid mutations is/are one or more point mutations.

12. The method of claim 1, wherein the cell used in the method is optimized for the phenotype prior to mutating the global transcription machinery.

13. The method of claim 1, wherein the global transcription machinery comprises more than one nucleic acid and/or polypeptide or is encoded by more than one nucleic acid.

* * * * *

SEQUENCE LISTING

```
<160> NUMBER OF SEQ ID NOS: 27

<210> SEQ ID NO 1
<211> LENGTH: 44
<212> TYPE: DNA
<213> ORGANISM: Artificial
<220> FEATURE:
<223> OTHER INFORMATION: Primer CM_sense_AhdI

<400> SEQUENCE: 1
gttgcctgac tccccgtcgc caggcgttta agggcaccaa taac                44

<210> SEQ ID NO 2
<211> LENGTH: 32
<212> TYPE: DNA
<213> ORGANISM: Artificial
```

```
<220> FEATURE:
<223> OTHER INFORMATION: Primer CM_anti_AatII

<400> SEQUENCE: 2
cagaagccac tggagcacct caaaactgca gt                                    32

<210> SEQ ID NO 3
<211> LENGTH: 34
<212> TYPE: DNA
<213> ORGANISM: Artificial
<220> FEATURE:
<223> OTHER INFORMATION: Primer pSC_sense_AflIII

<400> SEQUENCE: 3
cccacatgtc ctagacctag ctgcaggtcg agga                                  34

<210> SEQ ID NO 4
<211> LENGTH: 53
<212> TYPE: DNA
<213> ORGANISM: Artificial
<220> FEATURE:
<223> OTHER INFORMATION: Primer pSC_anti_NotI

<400> SEQUENCE: 4
aaggaaaaaa gcggccgcac gggtaagcct gttgatgata ccgctgcctt act             53

<210> SEQ ID NO 5
<211> LENGTH: 41
<212> TYPE: DNA
<213> ORGANISM: Artificial
<220> FEATURE:
<223> OTHER INFORMATION: Primer rpoD_sense_SacI

<400> SEQUENCE: 5
aacctaggag ctctgattta acggcttaag tgccgaagag c                          41

<210> SEQ ID NO 6
<211> LENGTH: 37
<212> TYPE: DNA
<213> ORGANISM: Artificial
<220> FEATURE:
<223> OTHER INFORMATION: Primer rpoD_anti_HindIII

<400> SEQUENCE: 6
tggaagcttt aacgcctgat ccggcctacc gattaat                               37

<210> SEQ ID NO 7
<211> LENGTH: 23
<212> TYPE: DNA
<213> ORGANISM: Artificial
<220> FEATURE:
<223> OTHER INFORMATION: Sequencing primer S1

<400> SEQUENCE: 7
ccatatgcgg tgtgaaatac cgc                                              23

<210> SEQ ID NO 8
<211> LENGTH: 24
<212> TYPE: DNA
<213> ORGANISM: Artificial
<220> FEATURE:
<223> OTHER INFORMATION: Sequencing primer S2

<400> SEQUENCE: 8
cacagctgaa acttcttgtc accc                                             24
```

```
<210> SEQ ID NO 9
<211> LENGTH: 22
<212> TYPE: DNA
<213> ORGANISM: Artificial
<220> FEATURE:
<223> OTHER INFORMATION: Sequencing primer S3

<400> SEQUENCE: 9
ttgttgaccc gaacgcagaa ga                                             22

<210> SEQ ID NO 10
<211> LENGTH: 20
<212> TYPE: DNA
<213> ORGANISM: Artificial
<220> FEATURE:
<223> OTHER INFORMATION: Sequencing primer S4

<400> SEQUENCE: 10
agaaaccggc ctgaccatcg                                                20

<210> SEQ ID NO 11
<211> LENGTH: 24
<212> TYPE: DNA
<213> ORGANISM: Artificial
<220> FEATURE:
<223> OTHER INFORMATION: Sequencing primer A1

<400> SEQUENCE: 11
gcttcgatct gacggatacg ttcg                                           24

<210> SEQ ID NO 12
<211> LENGTH: 24
<212> TYPE: DNA
<213> ORGANISM: Artificial
<220> FEATURE:
<223> OTHER INFORMATION: Sequencing primer A2

<400> SEQUENCE: 12
caggttgcgt aggtggagaa cttg                                           24

<210> SEQ ID NO 13
<211> LENGTH: 22
<212> TYPE: DNA
<213> ORGANISM: Artificial
<220> FEATURE:
<223> OTHER INFORMATION: Sequencing primer A3

<400> SEQUENCE: 13
gtgactgcga cctttcgctt tg                                             22

<210> SEQ ID NO 14
<211> LENGTH: 20
<212> TYPE: DNA
<213> ORGANISM: Artificial
<220> FEATURE:
<223> OTHER INFORMATION: Sequencing primer A4

<400> SEQUENCE: 14
catcagatca tcggcatccg                                                20

<210> SEQ ID NO 15
<211> LENGTH: 19
<212> TYPE: DNA
<213> ORGANISM: Artificial
<220> FEATURE:
<223> OTHER INFORMATION: Sequencing primer A5
```

<400> SEQUENCE: 15
gcttcggcag catcttcgt                                                    19

<210> SEQ ID NO 16
<211> LENGTH: 21
<212> TYPE: DNA
<213> ORGANISM: Artificial
<220> FEATURE:
<223> OTHER INFORMATION: Sequencing primer A6

<400> SEQUENCE: 16
cggaagcgat cacctatctg c                                                 21

<210> SEQ ID NO 17
<211> LENGTH: 613
<212> TYPE: PRT
<213> ORGANISM: Escherichia coli

<400> SEQUENCE: 17

```
Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
            20                  25                  30

Glu Asp Ile Val Asp Ser Asp Gln Ile Glu Asp Ile Ile Gln Met Ile
        35                  40                  45

Asn Asp Met Gly Ile Gln Val Met Glu Glu Ala Pro Asp Ala Asp Asp
    50                  55                  60

Leu Met Leu Ala Glu Asn Thr Ala Asp Glu Ala Ala Glu Ala Ala
65                  70                  75                  80

Ala Gln Val Leu Ser Ser Val Glu Ser Glu Ile Gly Arg Thr Thr Asp
                85                  90                  95

Pro Val Arg Met Tyr Met Arg Glu Met Gly Thr Val Glu Leu Leu Thr
            100                 105                 110

Arg Glu Gly Glu Ile Asp Ile Ala Lys Arg Ile Glu Asp Gly Ile Asn
        115                 120                 125

Gln Val Gln Cys Ser Val Ala Glu Tyr Pro Glu Ala Ile Thr Tyr Leu
    130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Glu Asp Leu Ala Pro
                165                 170                 175

Thr Ala Thr His Val Gly Ser Glu Leu Ser Gln Glu Asp Leu Asp Asp
            180                 185                 190

Asp Glu Asp Glu Asp Glu Glu Asp Gly Asp Asp Asp Ser Ala Asp Asp
        195                 200                 205

Asp Asn Ser Ile Asp Pro Glu Leu Ala Arg Glu Lys Phe Ala Glu Leu
    210                 215                 220

Arg Ala Gln Tyr Val Val Thr Arg Asp Thr Ile Lys Ala Lys Gly Arg
225                 230                 235                 240

Ser His Ala Thr Ala Gln Glu Glu Ile Leu Lys Leu Ser Glu Val Phe
                245                 250                 255

Lys Gln Phe Arg Leu Val Pro Lys Gln Phe Asp Tyr Leu Val Asn Ser
            260                 265                 270

Met Arg Val Met Met Asp Arg Val Arg Thr Gln Glu Arg Leu Ile Met
        275                 280                 285
```

```
Lys Leu Cys Val Glu Gln Cys Lys Met Pro Lys Lys Asn Phe Ile Thr
    290                 295                 300
Leu Phe Thr Gly Asn Glu Thr Ser Asp Thr Trp Phe Asn Ala Ala Ile
305                 310                 315                 320
Ala Met Asn Lys Pro Trp Ser Glu Lys Leu His Asp Val Ser Glu Glu
                325                 330                 335
Val His Arg Ala Leu Gln Lys Leu Gln Gln Ile Glu Glu Thr Gly
            340                 345                 350
Leu Thr Ile Glu Gln Val Lys Asp Ile Asn Arg Arg Met Ser Ile Gly
        355                 360                 365
Glu Ala Lys Ala Arg Ala Lys Lys Glu Met Val Glu Ala Asn Leu
370                 375                 380
Arg Leu Val Ile Ser Ile Ala Lys Lys Tyr Thr Asn Arg Gly Leu Gln
385                 390                 395                 400
Phe Leu Asp Leu Ile Gln Glu Gly Asn Ile Gly Leu Met Lys Ala Val
                405                 410                 415
Asp Lys Phe Glu Tyr Arg Arg Gly Tyr Lys Phe Ser Thr Tyr Ala Thr
            420                 425                 430
Trp Trp Ile Arg Gln Ala Ile Thr Arg Ser Ile Ala Asp Gln Ala Arg
        435                 440                 445
Thr Ile Arg Ile Pro Val His Met Ile Glu Thr Ile Asn Lys Leu Asn
    450                 455                 460
Arg Ile Ser Arg Gln Met Leu Gln Glu Met Gly Arg Glu Pro Thr Pro
465                 470                 475                 480
Glu Glu Leu Ala Glu Arg Met Leu Met Pro Glu Asp Lys Ile Arg Lys
                485                 490                 495
Val Leu Lys Ile Ala Lys Glu Pro Ile Ser Met Glu Thr Pro Ile Gly
            500                 505                 510
Asp Asp Glu Asp Ser His Leu Gly Asp Phe Ile Glu Asp Thr Thr Leu
        515                 520                 525
Glu Leu Pro Leu Asp Ser Ala Thr Thr Glu Ser Leu Arg Ala Ala Thr
    530                 535                 540
His Asp Val Leu Ala Gly Leu Thr Ala Arg Glu Ala Lys Val Leu Arg
545                 550                 555                 560
Met Arg Phe Gly Ile Asp Met Asn Thr Asp Tyr Thr Leu Glu Glu Val
                565                 570                 575
Gly Lys Gln Phe Asp Val Thr Arg Glu Arg Ile Arg Gln Ile Glu Ala
            580                 585                 590
Lys Ala Leu Arg Lys Leu Arg His Pro Ser Arg Ser Glu Val Leu Arg
        595                 600                 605
Ser Phe Leu Asp Asp
    610

<210> SEQ ID NO 18
<211> LENGTH: 612
<212> TYPE: PRT
<213> ORGANISM: Escherichia coli

<400> SEQUENCE: 18

Met Glu Gln Asn Pro Gln Ser Gln Leu Lys Leu Leu Val Thr Arg Gly
1               5                   10                  15
Lys Glu Gln Gly Tyr Leu Thr Tyr Ala Glu Val Asn Asp Leu Leu Pro
            20                  25                  30
Glu Asp Ile Val Asp Asp Gln Ile Glu Asp Ile Ile Gln Met Ile Asn
        35                  40                  45
```

```
Asp Met Gly Ile Gln Val Met Glu Ala Ser Asp Ala Asp Leu
    50                  55                  60

Met Leu Ala Glu Asn Thr Ala Asp Glu Asp Ala Glu Ala Ala Ala
65                  70                  75                  80

Gln Val Leu Ser Ser Val Glu Ser Glu Ile Gly Arg Thr Ile Asp Pro
                    85                  90                  95

Val Arg Met Tyr Met Arg Glu Met Gly Thr Val Glu Leu Leu Thr Arg
                100                 105                 110

Glu Gly Glu Ile Asp Ile Ala Lys Arg Ile Glu Asp Gly Ile Asn Gln
            115                 120                 125

Val Gln Cys Ser Val Ala Glu Tyr Pro Glu Ala Ile Thr Tyr Leu Leu
    130                 135                 140

Glu Gln Tyr Asp Arg Val Glu Ala Glu Ala Arg Leu Ser Asp Leu
145                 150                 155                 160

Ile Thr Gly Phe Val Asp Pro Asn Ala Glu Glu Asp Leu Ala Pro Thr
                165                 170                 175

Ala Thr His Val Gly Ser Glu Leu Ser Gln Glu Asp Leu Asp Asp Asp
                180                 185                 190

Glu Asp Glu Asp Glu Glu Asp Gly Asp Gly Ser Ala Asp Asp Asp
            195                 200                 205

Asn Ser Ile Asp Pro Glu Leu Ala Arg Glu Lys Leu Ala Glu Leu Arg
    210                 215                 220

Ala Gln Tyr Val Val Thr Arg Asp Thr Ile Lys Ala Lys Gly Arg Ser
225                 230                 235                 240

His Ala Thr Ala Gln Glu Glu Phe Leu Lys Leu Ser Glu Val Phe Lys
                245                 250                 255

Gln Phe Arg Leu Val Pro Lys Gln Phe Asp Tyr Leu Val Asn Ser Met
                260                 265                 270

Arg Val Met Met Asp Arg Val Arg Thr Gln Glu Arg Leu Val Met Lys
            275                 280                 285

Leu Cys Val Glu Gln Cys Lys Met Pro Lys Lys Asn Phe Ile Thr Leu
    290                 295                 300

Phe Thr Gly Asn Glu Thr Ser Asp Thr Trp Phe Asn Ala Ala Ile Ala
305                 310                 315                 320

Met Asn Lys Pro Trp Ser Glu Lys Leu His Asp Val Ser Glu Val
                325                 330                 335

His Arg Ala Leu Gln Lys Leu Gln Gln Ile Glu Glu Glu Thr Gly Leu
            340                 345                 350

Thr Ile Glu Gln Val Lys Asp Ile Asn Arg Arg Met Ser Ile Gly Glu
    355                 360                 365

Ala Lys Ala Arg Arg Ala Lys Lys Glu Met Val Glu Ala Asn Leu Arg
    370                 375                 380

Leu Val Ile Ser Ile Ala Lys Lys Tyr Thr Asn Arg Gly Leu Gln Phe
385                 390                 395                 400

Leu Asp Leu Ile Gln Glu Gly Asn Ile Gly Leu Met Lys Ala Val Asp
                405                 410                 415

Lys Phe Glu Tyr Arg Arg Gly Tyr Lys Phe Ser Thr Tyr Ala Thr Trp
                420                 425                 430

Trp Ile Arg Gln Ala Ile Thr Arg Ser Ile Ala Asp Gln Ala Arg Thr
            435                 440                 445

Ile Arg Ile Pro Val His Met Ile Glu Thr Ile Asn Lys Leu Asn Arg
    450                 455                 460
```

```
Ile Ser Arg Gln Met Leu Gln Glu Met Gly Arg Glu Pro Thr Pro Glu
465                 470                 475                 480

Glu Leu Ala Glu Arg Met Leu Met Pro Glu Asp Lys Ile Arg Lys Val
                485                 490                 495

Leu Lys Ile Ala Lys Glu Pro Ile Ser Met Glu Thr Pro Val Gly Asp
            500                 505                 510

Asp Glu Asp Ser His Leu Gly Asp Phe Ile Glu Asp Thr Thr Leu Glu
            515                 520                 525

Leu Pro Leu Asp Ser Ala Thr Thr Glu Ser Leu Arg Ala Ala Thr His
        530                 535                 540

Asp Val Leu Ala Gly Leu Thr Ala Arg Glu Ala Lys Val Leu Arg Met
545                 550                 555                 560

Arg Phe Gly Ile Asp Met Asn Thr Asp Tyr Thr Leu Glu Glu Val Gly
                565                 570                 575

Lys Gln Phe Asp Val Thr Arg Glu Arg Ile Arg Gln Ile Glu Ala Lys
                580                 585                 590

Ala Leu Arg Lys Leu Arg His Pro Ser Cys Ser Glu Val Leu Arg Ser
            595                 600                 605

Phe Leu Asp Asp
    610

<210> SEQ ID NO 19
<211> LENGTH: 107
<212> TYPE: PRT
<213> ORGANISM: Escherichia coli

<400> SEQUENCE: 19

Met Glu Thr Pro Ile Gly Asp Asp Glu Asp Ser His Leu Gly Asp Phe
1               5                   10                  15

Ile Glu Asp Thr Thr Leu Glu Leu Pro Leu Asp Ser Ala Thr Thr Glu
                20                  25                  30

Ser Leu Arg Ala Ala Thr His Asp Val Leu Ala Gly Leu Thr Ala Arg
            35                  40                  45

Glu Ala Lys Val Leu Arg Met Arg Phe Gly Ile Asp Met Asn Thr Asp
        50                  55                  60

Tyr Thr Leu Glu Glu Val Gly Lys Gln Phe Asp Val Thr Arg Glu Arg
65                  70                  75                  80

Ile Arg Gln Ile Glu Ala Lys Ala Leu Arg Lys Leu Arg His Pro Ser
                85                  90                  95

Cys Ser Glu Val Leu Arg Ser Phe Leu Asp Asp
            100                 105

<210> SEQ ID NO 20
<211> LENGTH: 107
<212> TYPE: PRT
<213> ORGANISM: Escherichia coli

<400> SEQUENCE: 20

Met Glu Thr Pro Ile Gly Asp Asp Glu Ser Leu Leu Gly Asp Phe
1               5                   10                  15

Ile Glu Asp Thr Thr Leu Glu Leu Pro Leu Asp Ser Ala Thr Thr Val
                20                  25                  30

Ser Leu Arg Val Ala Thr His Asp Val Leu Ala Gly Leu Thr Ala Arg
            35                  40                  45

Val Ala Lys Val Leu Arg Met Arg Phe Gly Ile Asn Met Asn Thr Asp
        50                  55                  60
```

```
Tyr Thr Leu Glu Glu Val Gly Lys Gln Phe Asp Val Thr Arg Glu Arg
 65                  70                  75                  80

Ile Arg Gln Ile Glu Ala Lys Ala Leu Arg Lys Leu Arg His Pro Ser
                 85                  90                  95

Arg Ser Gly Val Gln Arg Ser Phe Leu Asp Asp
            100                 105
```

<210> SEQ ID NO 21
<211> LENGTH: 107
<212> TYPE: PRT
<213> ORGANISM: Escherichia coli

<400> SEQUENCE: 21

```
Met Glu Thr Pro Ile Gly Asp Asp Glu Asp Ser His Leu Gly Asp Tyr
  1               5                  10                  15

Ile Glu Asp Thr Thr Leu Glu Leu Pro Leu Asp Ser Ala Thr Thr Glu
                 20                  25                  30

Ser Leu Arg Ala Ala Thr His Asp Val Leu Ala Gly Met Thr Ala Arg
             35                  40                  45

Glu Ala Lys Val Leu Arg Met Arg Phe Gly Ile Asp Val Asn Thr Asp
 50                  55                  60

Tyr Thr Leu Glu Glu Val Gly Lys Gln Phe Asp Val Thr Arg Glu Arg
 65                  70                  75                  80

Ile Ser Gln Ile Glu Ala Lys Ala Leu Arg Lys Leu Arg His Pro Ser
                 85                  90                  95

Arg Ser Glu Val Leu Arg Ser Phe Leu Asp Asp
            100                 105
```

<210> SEQ ID NO 22
<211> LENGTH: 612
<212> TYPE: PRT
<213> ORGANISM: Escherichia coli

<400> SEQUENCE: 22

```
Met Glu Gln Asn Pro Gln Ser Gln Leu Lys Leu Leu Val Thr Arg Gly
  1               5                  10                  15

Lys Glu Gly Tyr Leu Thr Tyr Ala Glu Val Asn Asp His Leu Pro Glu
                 20                  25                  30

Asp Ile Val Asp Ser Asp Gln Ile Glu Asp Ile Ile Gln Met Ile Asn
             35                  40                  45

Asp Met Gly Ile Gln Val Met Glu Glu Ala Pro Asp Ala Asp Asp Leu
 50                  55                  60

Met Leu Ala Glu Asn Thr Ala Asp Glu Asp Ala Ala Glu Ala Ala Ala
 65                  70                  75                  80

Gln Val Leu Ser Ser Val Glu Ser Gly Val Gly Arg Thr Thr Asp Pro
                 85                  90                  95

Val Arg Met Tyr Met Arg Glu Met Gly Thr Val Glu Leu Leu Thr Arg
            100                 105                 110

Glu Gly Glu Ile Asp Ile Ala Lys Arg Ile Glu Asp Gly Asn Asn Gln
            115                 120                 125

Val Gln Cys Ser Val Ala Glu Tyr Pro Glu Ala Ile Thr Tyr Leu Leu
            130                 135                 140

Glu Gln Tyr Asp Arg Ala Glu Ala Glu Ala Arg Leu Ser Asp Met
145                 150                 155                 160

Ile Thr Gly Phe Val Asp Pro Asn Ala Glu Glu Asp Leu Ala Pro Thr
                165                 170                 175
```

```
Ala Thr His Val Gly Ser Glu Leu Ser Gln Asp Leu Asp Asp
            180                 185                 190
Glu Asp Glu Asp Glu Val Asp Gly Asp Asp Ser Ala Asp Asp
        195                 200                 205
Asn Ser Ile Asp Pro Glu Leu Ala Arg Glu Lys Phe Ala Glu Leu Arg
    210                 215                 220
Ala Gln Tyr Val Val Thr Arg Asp Thr Ile Lys Ala Lys Gly Arg Ser
225                 230                 235                 240
His Ala Thr Ala Gln Glu Glu Ile Leu Lys Leu Ser Glu Val Phe Lys
                245                 250                 255
Gln Phe Arg Leu Val Pro Lys Gln Phe Asp Tyr Leu Val Asn Ser Met
            260                 265                 270
Arg Val Met Met Asp His Val Arg Thr Gln Glu Arg Leu Ile Met Lys
            275                 280                 285
Leu Cys Val Glu Gln Cys Lys Met Pro Lys Lys Asn Phe Ile Thr Leu
        290                 295                 300
Phe Thr Gly Asn Glu Thr Ser Asp Thr Trp Phe Asn Ala Ala Ile Ala
305                 310                 315                 320
Met Asn Arg Pro Trp Ser Glu Lys Leu His Asp Val Ser Glu Val
                325                 330                 335
His Arg Ala Leu Gln Lys Leu Gln Gln Ile Glu Glu Thr Gly Leu
            340                 345                 350
Thr Ile Glu Gln Val Lys Asp Ile Asn Arg Arg Met Ser Ile Gly Glu
            355                 360                 365
Ala Lys Ala Arg Arg Ala Lys Lys Glu Met Val Glu Ala Asn Leu Arg
370                 375                 380
Leu Val Ile Ser Ile Ala Lys Lys Tyr Thr Asn Arg Gly Leu Gln Phe
385                 390                 395                 400
Leu Asp Leu Ile Gln Glu Gly Asn Ile Gly Leu Met Lys Ala Val Asp
                405                 410                 415
Lys Phe Glu Tyr Arg Arg Gly Tyr Lys Phe Ser Thr Tyr Ala Thr Trp
            420                 425                 430
Trp Ile Arg Gln Ala Ile Thr Arg Ser Ile Ala Asp Gln Ala Arg Thr
            435                 440                 445
Ile Arg Ile Pro Val His Met Ile Glu Thr Ile Asn Lys Leu Asn Arg
    450                 455                 460
Ile Ser Arg Gln Met Leu Gln Glu Met Gly Arg Glu Pro Thr Pro Glu
465                 470                 475                 480
Glu Leu Ala Glu Arg Met Leu Met Pro Glu Asp Lys Ile Arg Lys Val
                485                 490                 495
Leu Lys Ile Ala Lys Glu Pro Ile Ser Met Glu Thr Pro Ile Gly Asp
            500                 505                 510
Asp Glu Asp Ser His Leu Gly Asp Phe Ile Glu Asp Thr Thr Leu Glu
        515                 520                 525
Leu Pro Leu Asp Ser Ala Thr Thr Glu Ser Leu Arg Ala Ala Thr His
    530                 535                 540
Asp Val Leu Ala Gly Leu Thr Ala Arg Glu Ala Lys Val Leu Arg Met
545                 550                 555                 560
Arg Phe Gly Ile Asp Met Asn Thr Asp Tyr Thr Leu Glu Glu Val Gly
                565                 570                 575
Lys Gln Phe Asp Val Thr Arg Glu Arg Ile Arg Gln Ile Glu Ala Lys
            580                 585                 590
Ala Leu Arg Lys Leu Arg His Pro Ser Arg Ser Glu Val Leu Arg Ser
```

-continued

```
                 595                 600                 605

Phe Leu Asp Asp
    610

<210> SEQ ID NO 23
<211> LENGTH: 613
<212> TYPE: PRT
<213> ORGANISM: Escherichia coli

<400> SEQUENCE: 23

Met Asp Gln Asn Pro Gln Ser Gln Leu Lys Leu Val Thr Arg Gly
1               5                   10                  15

Lys Glu Gln Gly Tyr Leu Thr Tyr Ala Glu Val Asn Asp His Leu Pro
                20                  25                  30

Glu Asp Ile Val Asp Ser Asp Gln Ile Glu Asp Ile Ile Gln Met Ile
            35                  40                  45

Asn Asp Met Gly Ile Gln Val Met Glu Glu Ala Pro Asp Ala Asp Asp
        50                  55                  60

Leu Met Leu Ala Glu Asn Thr Ala Asp Glu Asp Ala Ala Glu Ala Val
65                  70                  75                  80

Ala Gln Val Leu Ser Ser Val Glu Ser Glu Ile Gly Arg Thr Thr Asp
                85                  90                  95

Pro Val Arg Met Tyr Met Arg Glu Met Gly Thr Val Glu Leu Leu Thr
            100                 105                 110

Arg Glu Gly Glu Ile Asp Ile Ala Lys Arg Ile Glu Asp Gly Ile Asn
        115                 120                 125

Gln Val Gln Cys Ser Val Ala Glu Tyr Pro Glu Ala Ile Thr Tyr Leu
    130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Glu Asp Leu Ala Pro
                165                 170                 175

Thr Ala Thr His Val Gly Ser Glu Pro Ser Gln Glu Asp Leu Asp Asp
            180                 185                 190

Asp Glu Asp Glu Asp Glu Asp Gly Asp Asp Ser Ala Asp Asp
        195                 200                 205

Asp Asn Ser Ile Asp Pro Glu Leu Ala Arg Glu Lys Phe Ala Glu Leu
    210                 215                 220

Arg Ala Gln Tyr Val Val Thr Arg Asp Thr Ile Lys Ala Lys Gly Arg
225                 230                 235                 240

Ser His Ala Thr Ala Gln Glu Glu Ile Leu Lys Leu Ser Glu Val Phe
                245                 250                 255

Lys Gln Phe Arg Leu Val Pro Lys Gln Phe Asp Tyr Leu Val Asn Ser
            260                 265                 270

Met Arg Val Met Met Asp Arg Val Arg Thr Gln Glu Arg Leu Ile Met
        275                 280                 285

Lys Leu Cys Val Glu Gln Cys Lys Met Pro Lys Lys Asn Phe Ile Thr
    290                 295                 300

Leu Phe Thr Gly Asn Glu Thr Ser Asp Thr Trp Phe Asn Ala Ala Ile
305                 310                 315                 320

Ala Met Asn Lys Leu Trp Ser Glu Lys Leu His Asp Val Ser Glu Glu
                325                 330                 335

Val His Arg Ala Leu Gln Lys Leu Arg Gln Ile Glu Glu Glu Thr Gly
            340                 345                 350
```

```
Leu Thr Ile Glu Gln Val Lys Asp Ile Asn Arg Arg Met Ser Ile Gly
            355                 360                 365

Glu Ala Lys Ala Arg Arg Ala Lys Lys Glu Met Val Glu Ala Asn Leu
        370                 375                 380

Arg Leu Val Ile Ser Ile Ala Lys Lys Tyr Thr Asn Arg Gly Leu Gln
385                 390                 395                 400

Phe Leu Asp Leu Ile Gln Glu Gly Asn Ile Gly Leu Met Lys Ala Val
                405                 410                 415

Asp Lys Phe Glu Tyr Arg Arg Gly Tyr Lys Phe Ser Thr Tyr Ala Thr
            420                 425                 430

Trp Trp Ile Arg Gln Ala Ile Thr Arg Phe Ile Ala Asp Gln Ala Arg
        435                 440                 445

Thr Ile Arg Ile Pro Val His Met Ile Glu Thr Ile Asn Lys Leu Asn
    450                 455                 460

Arg Ile Ser Arg Gln Met Leu Gln Glu Met Gly Arg Glu Pro Thr Pro
465                 470                 475                 480

Glu Glu Leu Ala Glu Arg Met Leu Met Pro Glu Asp Lys Ile Arg Lys
                485                 490                 495

Val Leu Lys Ile Ala Lys Glu Pro Ile Ser Met Glu Thr Pro Ile Gly
            500                 505                 510

Asp Asp Glu Asp Ser His Leu Gly Asp Phe Ile Glu Asp Thr Thr Leu
        515                 520                 525

Glu Leu Pro Leu Asp Ser Ala Thr Thr Glu Ser Leu Arg Ala Ala Thr
    530                 535                 540

His Asp Val Leu Ala Gly Leu Thr Ala Arg Glu Ala Lys Val Leu Arg
545                 550                 555                 560

Met Arg Phe Gly Ile Asp Val Asn Thr Asp Tyr Thr Leu Glu Glu Val
                565                 570                 575

Ser Lys Gln Phe Asn Val Thr Arg Glu Arg Ile Arg Gln Ile Glu Ala
            580                 585                 590

Lys Ala Leu Arg Lys Leu Arg His Pro Ser Arg Ser Asp Val Leu Arg
        595                 600                 605

Ser Phe Leu Asp Asp
    610

<210> SEQ ID NO 24
<211> LENGTH: 611
<212> TYPE: PRT
<213> ORGANISM: Escherichia coli

<400> SEQUENCE: 24

Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
            20                  25                  30

Glu Asp Ile Val Asp Ser Asp Gln Ile Glu Asp Ile Ile Gln Met Ile
        35                  40                  45

Asn Asp Met Gly Ile Gln Val Met Glu Glu Ala Pro Asp Ala Asp Asp
    50                  55                  60

Leu Met Leu Ala Glu Asn Thr Ala Asp Glu Asp Ala Ala Glu Ala Ala
65                  70                  75                  80

Ala Gln Val Leu Ser Ser Val Glu Ser Glu Ile Gly Arg Thr Thr Asp
                85                  90                  95

Pro Val Arg Met Tyr Met Arg Glu Met Gly Thr Val Glu Leu Leu Thr
            100                 105                 110
```

```
Arg Glu Gly Glu Ile Asp Ile Ala Lys Arg Ile Glu Asp Gly Val Asn
            115                 120                 125

Gln Val Gln Cys Ser Val Ala Glu Tyr Pro Glu Ala Ile Thr Tyr Leu
        130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Glu Asp Leu Ala Pro
                165                 170                 175

Thr Ala Thr His Val Gly Ser Glu Leu Ser Gln Glu Asp Leu Asp Asp
                180                 185                 190

Asp Glu Asp Glu Asp Glu Asp Gly Asp Asp Ser Ala Asp Asp
                195                 200                 205

Asp Asn Ser Ile Asp Pro Glu Leu Ala Arg Glu Lys Phe Ala Glu Leu
            210                 215                 220

Arg Ala Gln Tyr Val Val Thr Arg Asp Thr Ile Ala Lys Gly Arg Ser
225                 230                 235                 240

His Ala Thr Ala Gln Glu Ile Leu Lys Leu Ser Glu Val Phe Lys
                245                 250                 255

Gln Phe Arg Leu Val Pro Lys Gln Phe Asp Tyr Leu Val Asn Ser Met
            260                 265                 270

Arg Val Met Met Asp Arg Val Arg Thr Gln Glu Arg Leu Ile Met Lys
            275                 280                 285

Leu Cys Val Glu Gln Cys Lys Met Pro Lys Lys Asn Phe Ile Thr Leu
        290                 295                 300

Phe Thr Gly Asn Glu Thr Ser Asp Thr Trp Phe Asn Ala Ala Ile Ala
305                 310                 315                 320

Met Asn Lys Pro Trp Ser Glu Lys Leu His Asp Val Ser Glu Val
                325                 330                 335

His Arg Ala Leu Gln Lys Leu Gln Gln Ile Glu Glu Thr Gly Leu
                340                 345                 350

Thr Ile Glu Gln Val Lys Asp Ile Asn Arg Arg Met Ser Ile Gly Glu
        355                 360                 365

Ala Lys Ala Arg Arg Ala Lys Lys Glu Met Val Glu Ala Asn Leu Arg
        370                 375                 380

Leu Val Ile Ser Ile Ala Lys Lys Phe Thr Asn Arg Gly Leu Gln Phe
385                 390                 395                 400

Leu Asp Leu Ile Gln Glu Gly Asn Ile Gly Leu Val Lys Ala Val Asp
                405                 410                 415

Lys Phe Glu Tyr Arg Arg Gly Tyr Lys Phe Ser Thr Tyr Ala Thr Trp
            420                 425                 430

Trp Ile Arg Gln Ala Ile Thr Arg Ser Ile Ala Asp Gln Ala Arg Thr
        435                 440                 445

Ile Arg Ile Pro Val His Met Ile Glu Thr Ile Asn Leu Asn Arg Ile
450                 455                 460

Ser Arg Gln Met Leu Gln Glu Met Gly Arg Glu Pro Thr Pro Glu Glu
465                 470                 475                 480

Leu Ala Glu Arg Met Leu Met Gln Glu Asp Lys Ile Arg Lys Val Leu
                485                 490                 495

Lys Ile Ala Asn Glu Pro Ile Ser Met Glu Thr Pro Ile Gly Asp Asp
                500                 505                 510

Glu Asp Ser His Leu Gly Asp Phe Ile Glu Asp Thr Thr Leu Glu Leu
            515                 520                 525
```

```
Pro Leu Asp Ser Ala Thr Thr Glu Ser Leu Arg Ala Ala Thr His Asp
    530                 535                 540

Val Leu Ala Gly Leu Thr Ala Arg Glu Ala Lys Val Leu Arg Met Arg
545                 550                 555                 560

Phe Gly Ile Asp Met Asn Thr Asp Tyr Thr Leu Glu Glu Val Gly Lys
                565                 570                 575

Gln Phe Asp Val Thr Arg Glu Arg Ile Arg Gln Ile Glu Ala Lys Ala
            580                 585                 590

Leu Arg Lys Leu Arg His Pro Ser Arg Pro Glu Val Leu Arg Ser Phe
        595                 600                 605

Leu Asp Asp
    610

<210> SEQ ID NO 25
<211> LENGTH: 613
<212> TYPE: PRT
<213> ORGANISM: Escherichia coli

<400> SEQUENCE: 25

Met Glu Gln Asn Pro Gln Ser Gln Leu Lys Leu Leu Val Thr Arg Gly
1               5                   10                  15

Lys Glu Gln Gly Tyr Leu Thr Tyr Ala Glu Val Asn Asp His Leu Pro
            20                  25                  30

Glu Asp Ile Val Asp Ser Asp Gln Ile Glu Asp Ile Gln Met Ile
        35                  40                  45

Asn Asp Met Gly Ile Gln Val Met Glu Glu Ala Pro Asp Ala Asp Asp
50                  55                  60

Leu Met Leu Ala Glu Asn Thr Ala Asp Glu Asp Ala Ala Glu Ala Ala
65                  70                  75                  80

Ala Gln Val Leu Ser Ser Val Glu Ser Glu Ile Gly Arg Thr Thr Asp
                85                  90                  95

Pro Val Arg Met Tyr Met Arg Glu Met Gly Thr Val Glu Leu Leu Thr
            100                 105                 110

Arg Glu Gly Glu Ile Asp Ile Ala Lys Arg Ile Glu Asp Gly Ile Asn
        115                 120                 125

Gln Val Gln Cys Ser Val Ala Glu Tyr Pro Glu Ala Ile Thr Tyr Leu
    130                 135                 140

Leu Glu Gln Tyr Asp Arg Val Glu Ala Glu Ala Arg Leu Ser Asp
145                 150                 155                 160

Leu Ile Thr Gly Phe Val Asp Pro Asn Ala Glu Glu Asp Leu Ala Pro
                165                 170                 175

Thr Ala Thr His Val Gly Ser Glu Leu Ser Gln Glu Asp Leu Asp Asp
            180                 185                 190

Asp Glu Asp Glu Asp Glu Asp Gly Asp Asp Ser Ala Asp Asp
        195                 200                 205

Asp Asn Ser Ile Asp Pro Glu Leu Ala Arg Glu Lys Phe Ala Glu Leu
    210                 215                 220

Arg Ala Gln Tyr Val Val Thr Arg Asp Thr Ile Lys Ala Lys Gly Arg
225                 230                 235                 240

Ser His Ala Thr Ala Gln Glu Glu Ile Leu Lys Leu Ser Glu Val Phe
                245                 250                 255

Lys Gln Phe Arg Leu Val Pro Lys Gln Phe Asp Tyr Leu Val Asn Ser
            260                 265                 270

Met Arg Val Met Met Asp Arg Val Arg Thr Gln Glu Arg Leu Ile Met
        275                 280                 285
```

Lys Leu Cys Val Glu Gln Cys Lys Met Pro Lys Asn Phe Ile Thr
290                 295                 300

Leu Phe Thr Gly Asn Glu Thr Ser Asp Thr Trp Phe Asn Ala Ala Ile
305                 310                 315                 320

Ala Met Asn Lys Pro Trp Ser Glu Lys Leu His Asp Val Ser Glu Glu
                325                 330                 335

Val His Arg Ala Leu Gln Lys Leu Gln Gln Ile Glu Glu Thr Gly
                340                 345                 350

Leu Thr Ile Glu Gln Val Lys Asp Ile Asn Arg Arg Met Ser Ile Gly
            355                 360                 365

Glu Ala Lys Ala Arg Arg Ala Lys Lys Glu Met Val Glu Ala Asn Leu
370                 375                 380

Arg Leu Val Ile Ser Ile Ala Lys Lys Tyr Thr Asn Arg Gly Leu Gln
385                 390                 395                 400

Phe Leu Asp Leu Ile Gln Glu Gly Tyr Ile Gly Leu Met Lys Ala Val
                405                 410                 415

Asp Lys Phe Glu Tyr Arg Arg Gly Tyr Lys Phe Ser Thr Tyr Ala Thr
                420                 425                 430

Trp Trp Ile Arg Gln Ala Ile Thr Arg Ser Ile Ala Asp Gln Ala Arg
            435                 440                 445

Thr Ile Arg Ile Pro Val His Met Ile Glu Thr Ile Asp Lys Leu Asn
450                 455                 460

Arg Ile Ser Arg Gln Met Leu Gln Glu Met Gly Arg Glu Pro Thr Pro
465                 470                 475                 480

Glu Glu Leu Ala Glu Arg Met Leu Met Pro Glu Asp Lys Ile Arg Lys
                485                 490                 495

Val Leu Lys Ile Ala Lys Glu Pro Ile Ser Met Glu Thr Pro Ile Gly
            500                 505                 510

Asp Asp Glu Asp Ser His Leu Gly Asp Phe Ile Glu Asp Thr Thr Leu
515                 520                 525

Glu Leu Pro Leu Asp Ser Ala Thr Thr Glu Ser Leu Arg Ala Ala Thr
530                 535                 540

His Asp Val Leu Ala Gly Leu Thr Ala Arg Glu Ala Lys Val Leu Arg
545                 550                 555                 560

Met Arg Phe Gly Ile Asp Met Asn Thr Asp Tyr Thr Leu Glu Glu Val
                565                 570                 575

Gly Lys Gln Phe Asp Val Thr Arg Glu Arg Ile Arg Gln Ile Glu Ala
            580                 585                 590

Lys Ala Leu Arg Lys Leu Arg His Pro Ser Arg Ser Glu Val Leu Arg
595                 600                 605

Ser Phe Leu Asp Asp
    610

<210> SEQ ID NO 26
<211> LENGTH: 107
<212> TYPE: PRT
<213> ORGANISM: Escherichia coli

<400> SEQUENCE: 26

Met Glu Thr Pro Ile Gly Asp Asp Glu Asp Pro His Leu Gly Asp Phe
1               5                   10                  15

Ile Glu Asp Thr Thr Leu Glu Leu Pro Leu Val Ser Ala Thr Thr Val
                20                  25                  30

Ser Leu Arg Ala Ala Thr His Asp Val Leu Ala Gly Gln Thr Ala Arg

```
              35                  40                  45
Glu Ala Lys Val Leu Arg Met Arg Phe Gly Val Asp Met Asn Thr Asp
    50                  55                  60

Tyr Thr Leu Glu Glu Val Gly Lys Gln Phe Asp Val Thr Arg Val Arg
65                  70                  75                  80

Ile Arg Gln Ile Glu Ala Lys Ala Leu Arg Lys Leu Arg His Pro Ser
                85                  90                  95

Arg Ser Glu Val Leu Arg Ser Phe Leu Asp Asp
            100                 105

<210> SEQ ID NO 27
<211> LENGTH: 2062
<212> TYPE: DNA
<213> ORGANISM: Escherichia coli

<400> SEQUENCE: 27
tgatttaacg gcttaagtgc cgaagagcga tcgggaagcc cccgacagcc gcactgagag      60
gcagcggcaa atatataagt acgccctcgt aattatcgtt ggcggtaaac aaccgttgga     120
tttcagcgtt aacggctgaa ggacatcggt caatcgccc aacaccaacc tcatgaaata     180
agtgtggata ccgtcttatg gagcaaaacc cgcagtcaca gctgaaactt cttgtcaccc     240
gtggtaagga gcaaggctat ctgacctatg ccgaggtcaa tgaccatctg ccggaagata     300
tcgtcgattc agatcagatc gaagacatca tccaaatgat caacgacatg gcattcagg     360 tgatggaaga agcaccggat gccgatgatc tgatgctggc tgaaaacacc gcggacgaag     420
atgctgccga agccgccgcg caggtgcttt ccagcgtgga atctgaaatc gggcgcacga     480
ctgacccggt acgcatgtac atgcgtgaaa tgggcaccgt tgaactgttg acccgcgaag     540
gcgaaattga catcgctaag cgtattgaag acgggatcaa ccaggttcaa tgctccgttg     600
ctgaatatcc ggaagcgatc acctatctgc tggaacagta cgatcgtgtt gaagcagaag     660
aagcgcgtct gtccgatctg atcaccggct ttgttgaccc gaacgcagaa aagatctgg     720 cacctaccgc cactcacgtc ggttctgagc tttcccagga agatctggac gatgacgaag     780
atgaagacga agaagatggc gatgacgaca gcgccgatga tgacaacagc atcgacccgg     840
aactggctcg cgaaaaattt gcggaactac gcgctcagta cgttgtaacg cgtgacacca     900
tcaaagcgaa aggtcgcagt cacgctaccg ctcaggaaga gatcctgaaa ctgtctgaag     960
tattcaaaca gttccgcctg gtgccgaagc agtttgacta cctggtcaac agcatgcgcg    1020
tcatgatgga ccgcgttcgt acgcaagaac gtctgatcat gaagctctgc gttgagcagt    1080
gcaaaatgcc gaagaaaaac ttcattaccc tgtttaccgg caacgaaacc agcgatacct    1140
ggttcaacgc ggcaattgcg atgaacaagc cgtggtcgga aaaactgcac gatgtctctg    1200
aagaagtgca tcgcgccctg caaaaactgc agcagattga agaagaaacc ggcctgacca    1260
tcgagcaggt taaagatatc aaccgtcgta tgtccatcgg tgaagcgaaa gcccgccgtg    1320
cgaagaaaga gatggttgaa gcgaacttac gtctggttat ttctatcgct aagaaataca    1380
ccaaccgtgg cttgcagttc cttgacctga ttcaggaagg caacatcggt ctgatgaaag    1440
cggttgataa attcgaatac cgccgtggtt acaagttctc cacctacgca acctggtgga    1500
tccgtcaggc gatcacccgc tctatcgcgg atcaggcgcg caccatccgt attccggtgc    1560
atatgattga ccatcaac aagctcaacc gtatttctcg ccagatgctg caagagatgg    1620
gccgtgaacc gacgccggaa gaactggctg aacgtatgct gatgccggaa gacaagatcc    1680
gcaaagtgct gaagatcgcc aaagagccaa tctccatgga aacgccgatc ggtgatgatg    1740
```

-continued

```
aagattcgca tctgggggat ttcatcgagg ataccaccct cgagctgccg ctggattctg    1800
cgaccaccga aagcctgcgt gcggcaacgc acgacgtgct ggctggcctg accgcgcgtg    1860
aagcaaaagt tctgcgtatg cgtttcggta tcgatatgaa caccgactac acgctggaag   1920
aagtgggtaa acagttcgac gttacccgcg aacgtatccg tcagatcgaa gcgaaggcgc   1980
tgcgcaaact gcgtcacccg agccgttctg aagtgctgcg tagcttcctg gacgattaat   2040
cggtaggccg gatcaggcgt ta                                            2062
```